United States Patent
Skouv et al.

(10) Patent No.: US 6,316,198 B1
(45) Date of Patent: Nov. 13, 2001

(54) DETECTION OF MUTATIONS IN GENES BY SPECIFIC LNA PRIMERS

(75) Inventors: Jan Skouv, Espergærde; Mogens Fenger, Copenhagen; Mogens Havsteen Jacobsen, Vanløse, all of (DK)

(73) Assignee: Exiqon A/S, Vedbaek (DK)

(*) Notice: Subject to any disclaimer, the term of this patent is extended or adjusted under 35 U.S.C. 154(b) by 0 days.

(21) Appl. No.: 09/528,115

(22) Filed: Mar. 18, 2000

Related U.S. Application Data

(60) Provisional application No. 60/127,354, filed on Apr. 1, 1999.

(30) Foreign Application Priority Data

Mar. 18, 1999 (DK) ............................................. 1999 00383

(51) Int. Cl.⁷ .............................. C12Q 1/68; C12P 19/34; C07H 21/02

(52) U.S. Cl. ........................... 435/6; 435/91.1; 435/91.2; 536/23.1; 536/24.3

(58) Field of Search .......................... 435/6, 91.1, 91.2; 536/23.1, 24.3

(56) References Cited

U.S. PATENT DOCUMENTS

| | | |
|---|---|---|
| 4,683,195 | 7/1987 | Mullis et al. ............................. 435/6 |
| 4,683,202 | 7/1987 | Mullis ..................................... 435/91 |
| 4,800,159 | 1/1989 | Mullis et al. ....................... 435/172.3 |
| 5,409,818 * | 4/1995 | Davey et al. ..................... 435/91.21 |
| 5,432,272 | 7/1995 | Benner ................................ 536/25.3 |
| 5,605,794 | 2/1997 | Rust et al. ............................... 435/6 |

FOREIGN PATENT DOCUMENTS

| | | |
|---|---|---|
| 0 324 474 | 7/1989 | (EP). |
| 0 332 435 | 9/1989 | (EP). |
| 0 333 465 | 9/1989 | (EP). |
| 0538194 B1 | 4/1999 | (EP). |
| WO 89/09835 | 10/1989 | (WO). |
| WO 96/17087 | 6/1996 | (WO). |
| WO 96/20212 | 7/1996 | (WO). |
| WO 96/31557 | 10/1996 | (WO). |
| WO98/22489 | 5/1998 | (WO). |
| WO98/39352 | 9/1998 | (WO). |
| WO99/14226 | 3/1999 | (WO). |

OTHER PUBLICATIONS

Gudibande et al, "Rapid, non–separation electrochemiluminescent DNA hybridization assays for PCR products, using 3' labelled oligonucleotide probes", Mol. Cell. Probes 6:495–503, Dec. 1992.*
Tarkoy et al., *Helv. Chim. Acta*, 76:481 (1993).
Tarkoy et al., *Angew. Chem., Int. Ed. Engl.*, 32:1432 (1993).
Egli et al., *J. Am. Chem. Soc.*, 115:5855 (1993).
Tarkoy et al., *Helv. Chim. Acta*, 77:716 (1994).
Bolli et al., *Angew. Chem., Int. Ed. Engl.*, 34:694 (1995).
Bolli et al., *Helv. Chim. Acta*, 78:2077 (1995).
Litten et al., *Bioorg. Med. Chem. Lett.*, 5:1231 (1995).
Litten et al., *Helv. Chim. Acta*, 79:1129 (1996).
Bolli et al., *Chem. Biol.*, 3:197 (1996).
Bolli et al., *Nucleic Acids. Res.*, 24:4660 (1996).
K.H. Altmann et al., *Tetrahedron Lett.*, 35::2331 (1994).
K. H. Altmann et al., *Tetrahedron Lett.*, 35:7625 (1994).
Marquez et al., *J. Med. Chem.*, 39:3739 (1996).
Ezzitouni et al., *J. Chem. Soc., Perkin Trans.*, 1:1073 (1997).
Jones et al., *J. Am. Chem. Soc.*, 115:9816 (1993).
Wang et al., *Bioorg. Med. Chem. Lett.*, 7: 229 (1997).
Yannopoulus et al., *Synlett*, 378 (1997).
CHIMA, 36th IUPAC Congress, organized by the Swiss Chemical Society. Poster No. SB–B4: Steffens, R. and Leumann Ch. Tricyclo–DNA: synthesis, enzymatic stability, and pairing properties.
Nielsen, Master Thesis (Odense University, Denmark), p. 67–71 (1995).
Youssefyeh et al., *J. Org. Chem.*, 44:1301 (1979).
Jones et al., *J. Org. Chem.*, 44:1309 (1979).
Yang et al., *Tetrahedron Lett.*, 33:37 (1992).
Thrane et al., *Tetrahedron*, 51:10389 (1995).
Nielsen et al., *Bioorg. Med. Chem.*, 3:1493 (1995).
Freier et al., *Nucleic Acid Research*, 25:4429–4443 (1997).
Haly et al., *SYNLETT*, 687–689 (1996).
Zou et al., *Tetrahedron Lett.*, 37:941–944 (1996).
Herdewijn., *Liebigs Ann.*, 1337–1348 (1996).
Obika et al., *Tetrahedron Lett.*, 39:5401–5404 (1998).
Obika et al., *Tetrahedron Lett.*, 38:8735–8738 (1997).
7th Antisense Symposium, Nov. 21–22, 1997. Poster No. 32 and 33: Obika, D.N.; Morio, K. and Imanishi, T. Synthesis and properties of oligonucleotides containing novel bicyclic nucleosides with a fixed N–form sugar puckering.
CHIMA, 36th IUPAC Congress, organized by the Swiss Chemical Society. Poster No. SB–B12: Egtger, A. and Leumann Ch. Designe, synthesis and properties of bicyclo [3.2.1]–amio nucleic acids. Undated.

(List continued on next page.)

*Primary Examiner*—Jeffrey Fredman
(74) *Attorney, Agent, or Firm*—Peter F. Corless; Edwards & Angell, LLP

(57) ABSTRACT

The present invention relates to a method of detecting variant nucleic acid whose nucleotide sequence differs from one another at a single (or more) position(s). The method uses a set of chimeric oligonucleotides containing DNA monomers and monomers of a novel class of DNA analogues, locked nucleic acid (LNA). LNA oligomers obey the Watson-Crick base-pairing rules and form duplexes that are significantly more stable than similar duplexes formed by DNA. The "allele-specific" LNA-containing oligonucleotides wherein the LNA nucleotide(s) are found at the 3' position can be extended by means of enzymes only where the nucleotide(s), which is/are terminal in direction of extension, is/are complementary to the corresponding nucleotides of the nucleic acid (of the one allele) to be detected. Thus discrimination between alleles without subsequent differential hybridization with labelled oligonucleotides is possible. The invention further relates to reagents for performing the methods as well as applications of the method.

48 Claims, 6 Drawing Sheets

OTHER PUBLICATIONS

Figure 1:
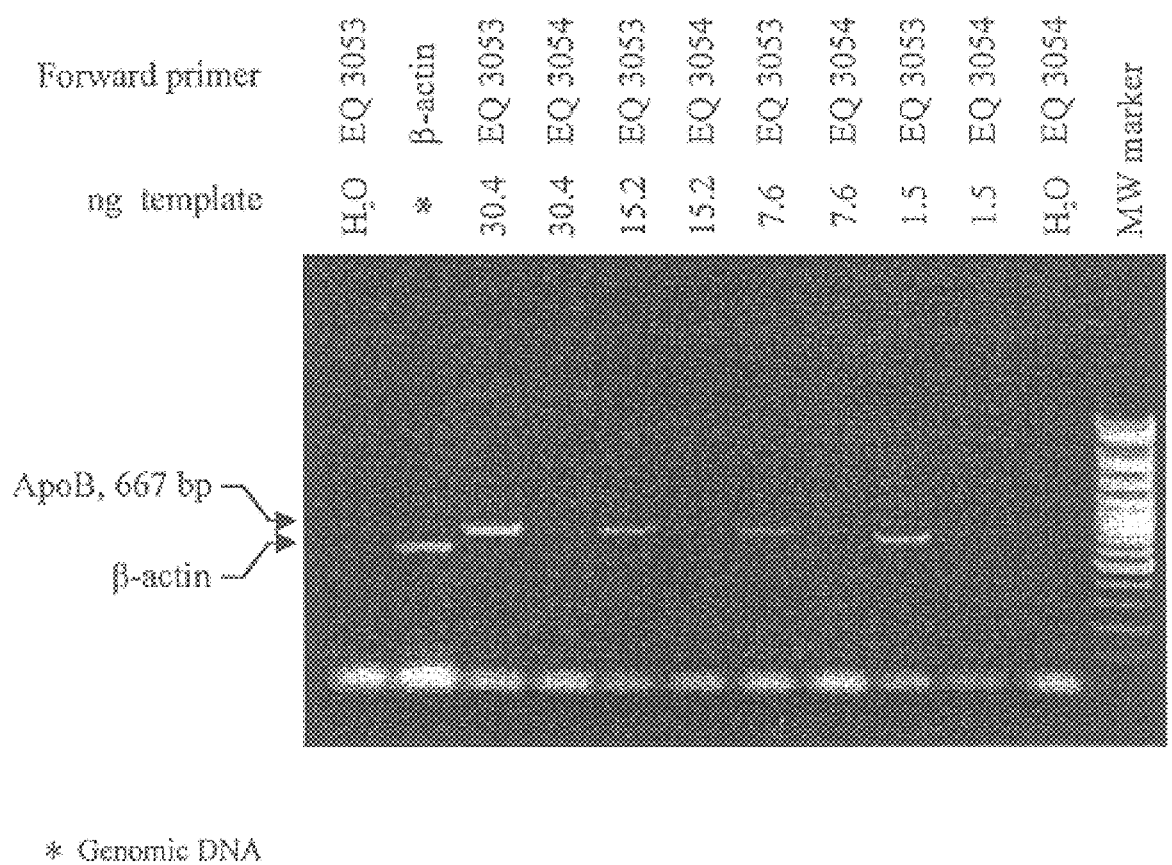

CHIMA, 36th IUPAC Congress, organized by the Swiss Chemical Society. Poster No. SB–B5: Epple, C. Ch., Pompizi, I. and Leumann Ch. Bicyclo [3.2.1]–DNA: an oligonucleotide analogue with a conformationally preorganized Phosphodiester backbone and a flexible sugar–base linkage. Undated.

Sep. 6–10, 1998: 13th International Round Table—Nucleoside, Nucleotides and their Biological Applications, Montpeilleir: Oral Communication 1: Wang, G. and Gunic, E. "Conformationally Locked Nucleoside Analogs. Synthesis of 2'–Deoxy–2'–C, 4'–Bridged Bicyclic Nucleoside".

Sep. 6–10, 1998: 13th International Round Table—Nucleoside, Nucleotides and their Biological Applications, Montpeilleir: Poster No. 288: Meldgaard, M. et al., "LNA (Locked Nucleic Acids): Synthesis and Thermal Denaturation Studies".

Sep. 6–10, 1998: 13th International Round Table—Nucleoside, Nucleotides and their Biological Applications, Montpeilleir: Poster No. 287 and Proceeding: Koshkin, A. A. et al., "Locked Nucleic Acids as synthetic RNA Mimics for Effective Complementary Recognition."

Sep. 6–10, 1998: 13th International Round Table—Nucleoside, Nucleotides and their Biological Applications, Montpeilleir: Poster No. 67: Nielsen, P. and Wengel, J. "A New Convergent Synthetic Approach Towards a–andβ–LNA (Locked Nucleic Acids)".

Oct. 8, 1998: Antisense 98, Targeting the Molecularl Basis of Disease: Poster No. 24: Havsteen, M. et al., "LNA (Locked Nucleic Acids): A new Class of High Affinity Nucleic Acids With Prime Potential as Antisense and Antigene Agents".

Jan. 21, 1998: National Seminar on Perspectives in Interfacial Areas of Chemistry and Biology, Delhi University: Wengel, J. "LNA (Locked Nucleic Acids): Synthesis and High Affinity Nucleic Acid Recognition—Stop the Twisting."

Marts. 27, 1998: Workshop of Young European Bioorganic Chemists, Munchen: Wengel, J. "LNA (Locked Nucleic Acids): Synthesis and High Affinity Nucleic Acid Recognition—Stop the Twisting."

Aug. 20, 1998: Arsmødet for Center for Medicinsk Bioteknologi, KVL: Wengel, J. "LNA (Locked Nucleic Acids)"ations, Montpeilleir: Oral Communication 1: Wang, G. and Gunic, E. "Conformationally Locked Nucleoside Analogs. Synthesis of 2'–Deoxy–2'–C, 4'–C–Bridged Bicyclic Nucleoside".

Sep. 7, 1998: 13th International Round Table—Nucleoside, Nucleotides and their Biological Applications, Montpeilleir: Oral Communication 2: Wengel, J. "LNA (locked Nucleic Acids)".

Sep. 8, 1998: Meeting in Lund, Sweden: Jakobsen, M. H. "LNA (Locked Nucleic Acids): A new Clas of High Affinity Nucleic Acids With Prime Potential as Antisense and Antigene Agents".

Nielsen et al., *J. Chem. Soc., Perkin Trans.*, 1:3423–3433 (1997).
Nielson et al., *Chem. Commun.*, 9:825–826 (1997).
Singh et al., *Chem. Commun.*, 455–456 (1998).
Koshkin et al., *Tetrahedron*, 54:36073630 (1998).
Koshkin et al., *Tetrahedron Lett.*, 39:4381–8384 (1998).
Singh et al., *Chem. Commun.*, 1237–1248 (1998).
Singh et al., *J. Org. Chem.*, 63:6078–6079 (1998).
Christensen et al., *J. Am. Chem. Soc.*, 120:5458–5463 (1998).
Koshkin et al., *J. Org. Chem.*, 63:2778–2781 (1998).
Kumar et al., *Bioorg. Med. Chem. Lett.*, 8:2219–2222 (1998).
Wengel et al., *Acc. Chem. Res.*, 32:301–310 (1999).
Koshkin et al., *J. Am. Chem. Soc.*, 120:13252–13253 (1998).
Singh et al., *J. Org. Chem.*, 10035–10039 (1998).
Nielsen et al., *Chem. Commun.*, 2645–2646 (1998).
Wengel et al., *Nucleosides Nucleoties*, 18:1365–1370 (1999).
Nielsen et al., *Nucleosides Nucleotides*, 18:701–702 (1999).
Kærno et al., *Chem. Commun.*, 657–658 (1999).
Rajwanshi et al., *J. Chem. Soc., Perkin Trans.*, 1:1407–1414 (1999).
Raunkjær et al., *J. Chem. Soc., Perkin Trans.*, 1:2543–2551 (1999).
Rajwanshi et al., *Chem. Commun.*, 1395–1396 (1999).
Pfundheller et al., *Nucleosides Nucleotides*, 18:2017–2030 (1999).
Rajwanshi et al., *Chem. Commun.*, 2073–2074 (1999).
Nielsen et al., *J. Biomol. Struc. Dyn.*, 17:175–191 (1999).
Nielsen et al., *Bioconjugate Chem.*, 11:228–238 (2000).
Rajwanshi et al., *Angewandte Chemie*, 39:1656–1659 (2000).
Minasov et al., *Biochemistry*, 39:3525 (2000).
Wahlesttedt et al., *Proc. Natl. Acad. Sci. USA*, 97:5633–5638 (2000).
Obika et al., *Tetrahedron Lett.*, 40:6465–6468 (1999).
Obika et al., *Tetrahedron Lett.*, 41:215–219 (1999).
Obika et al., *J. Chem. Soc., Chem. Commun.*, 2423–2424 (1999).
Wang et al., *Bioorg. Med. Chem. Lett.*, 9:1147–1150 (1999).
Obika et al., *Tetrahedron Lett.*, 41:221–224 (1999).
Obika et al., *Bioorg. Med. Chem. Lett.*, 9:515–518 (1999).
Obika et al., *Tetrahedron Lett.*, 39:5401–5405 (1998).
Imanishi et al., *J. Synth. Org. Chem.*, 57:959–980 (1999).
Chemical Abstracts, vol. 70, No. 1, Abstract No. 3737B (1969).
*Monatsch. Chem.*, 99(5):2111–2120 (1968).
Barany, *Proc. Natl. Acad. Sci. U.S.A.*, 88:189–193 (1991).
Bos et al., *Nature*, 327: 293–297 (1987).
Ehlen et al., *Biochem. Biophys. Res. Commun.*, 160:441–477 (1989).
Forrester et al., *Nature*, 327:298–303 (1987).
Gibbs et al., *Nucleic Acids Research*, 17(7):2437–2448 (1989).
Haliassos et al., *Nucl. Acids Res.*, 17(20):8093–8099 (1989).
Hermanson et al., Immobilized Affinity Ligand Techniques., Academic Press, San Diego, California, p. 137–ff (1992).
Koshkin et al., *Tetrahedron*, 54:3607–3630 (1998).
Kumar et al., *Oncogene Research*, 1;235–241 (1989).
Kwok et al., *Nucleic Acids Research*, 18:999–1005 (1990).
Larder et al., *Science*, 246:1155–1158 (1989).
Mesmaeker et al., Current Opinion in Structural Biology, 5, 343–355 (1995).
Nature Genetics, suppl. vol. 21, 1–60 (1999).
Soria et al., *Proc. Natl. Acad. Sci. U.S.A.*, 86:587–591 (1989).
Tybjaerg–Hansen et al., *Atherosclerosis*, 96:91–107 (1992).
Wood et al., *Proc. Natl. Acad. Sci., U.S.A.*, 82:1585–1588 (1985).
Wu et al., *Genomics*, 4:560–569 (1989).

* cited by examiner

A)

B)

C)

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Primer EQ 3053
<220> FEATURE:
<221> NAME/KEY: modified_base
<222> LOCATION: (25)...(25)
<223> OTHER INFORMATION: G LNA

<400> SEQUENCE: 1
cctacttgaa ttccaagagc acacg                                        25

<210> SEQ ID NO 2
<211> LENGTH: 25
<212> TYPE: DNA
<213> ORGANISM: Artificial Sequence
<220> FEATURE:
<223> OTHER INFORMATION: Primer EQ 3054
<220> FEATURE:
<221> NAME/KEY: modified_base
```

```
<222> LOCATION: (25)...(25)
<223> OTHER INFORMATION: A LNA

<400> SEQUENCE: 2
cctacttgaa ttccaagagc acaca                                   25

<210> SEQ ID NO 3
<211> LENGTH: 23
<212> TYPE: DNA
<213> ORGANISM: Artificial Sequence
<220> FEATURE:
<223> OTHER INFORMATION: Primer ApoBR2

<400> SEQUENCE: 3
tttagatcat ttagtttcag ccc                                     23

<210> SEQ ID NO 4
<211> LENGTH: 50
<212> TYPE: DNA
<213> ORGANISM: Human

<400> SEQUENCE: 4
cttacttgaa ttccaagagc acacggtctt cagtgaagct gcagggcact        50

<210> SEQ ID NO 5
<211> LENGTH: 50
<212> TYPE: DNA
<213> ORGANISM: Human

<400> SEQUENCE: 5
cttacttgaa ttccaagagc acacagtctt cagtgaagct gcagggcact        50

<210> SEQ ID NO 6
<211> LENGTH: 24
<212> TYPE: DNA
<213> ORGANISM: Artificial Sequence
<220> FEATURE:
<223> OTHER INFORMATION: Primer EQ 3213

<400> SEQUENCE: 6
gtttttcgta ctgtgctccc agag                                    24

<210> SEQ ID NO 7
<211> LENGTH: 22
<212> TYPE: DNA
<213> ORGANISM: Artificial Sequence
<220> FEATURE:
<223> OTHER INFORMATION: Primer EQ 3157
<220> FEATURE:
<221> NAME/KEY: modified_base
<222> LOCATION: (22)...(22)
<223> OTHER INFORMATION: T LNA

<400> SEQUENCE: 7
ccctgcagct tcactgaaga ct                                      22

<210> SEQ ID NO 8
<211> LENGTH: 23
<212> TYPE: DNA
<213> ORGANISM: Artificial Sequence
<220> FEATURE:
<223> OTHER INFORMATION: Primer EQ 3176

<400> SEQUENCE: 8
cacctcttac ttttccattg agt                                     23
```

```
<210> SEQ ID NO 9
<211> LENGTH: 25
<212> TYPE: DNA
<213> ORGANISM: Artificial Sequence
<220> FEATURE:
<223> OTHER INFORMATION: Primer EQ 3647

<400> SEQUENCE: 9
cctacttgaa ttccaagagc acacg                                              25
```

DETECTION OF MUTATIONS IN GENES BY SPECIFIC LNA PRIMERS

This application claims benefit of Prov. No. 60/127,354 filed Apr. 1, 1999.

FIELD OF THE INVENTION

The present invention comprises a method for detecting variant nucleic acids, a set of oligonucleotides suitable for this purpose, a reagent kit for performing the method of the invention and various uses and applications of the method in identifying specific gene sequences and diagnosing diseases and infections.

BACKGROUND OF THE INVENTION

Today, the testing of samples for the presence of certain nucleic acids in nucleic acid sequences gains increasingly more importance. This is partly due to the fact that the nucleotide sequence of a nucleic acid is a unique feature of each organism. First, a number of diseases are genetic in the sense that the nucleotide sequence for a "normal" gene is in some manner changed. Such a change could arise by the substitution of one base for another. Changes comprising more that one base can also be perceived. Given that three bases code for a single amino acid, a change in one base (a point mutation) could result in a change in the amino acid which, in turn, could result in a defective protein being made in a cell. Sickle cell anemia is a classic example of such a genetic defect caused by a change of a single base in a single gene; the beta-globin gene (A→T transversion at codon 6). Important point mutations can also be found for example in LDL receptors (Atherosclerosis (1992), 96:91–107) or in the apolipoprotein-B-gene (CGG→CAG mutation of codon 3500 (Proc. Natl. Acad. Sci. U.S.A. (1989) 86:587–591). Other examples of diseases caused by single gene defects include Factor IX and Factor VIII deficiency, breast cancer, cystic fibrosis, Factor V Leiden, Fragile X, Huntington disease, myotonic dystrophy, Haemophilia A, Haemophilia B, Neurofibromatosis type I, adenosine deaminase deficiency, purine nucleotide phosphorylase deficiency, ornithine transcarbamylase deficiency, argininsuccinate synthetase deficiency, beta-thalassemia, alpha-1 antitrypsin deficiency, glucocerebrosidase deficiency, phenylalanine hydroxylase deficiency and hypoxanthine-guanine phosphoribosyltransferase deficiency.

Second, the main cause of cancer is considered to be alterations in the cellular genes which directly or indirectly control cell growth and differentiation. There are at least thirty families of genes, called oncogenes, which are implicated in human tumor formation. Members of one such family, the ras gene family, are frequently found to be mutated in human tumors. In their normal state, proteins produced by the ras genes are thought to be involved in normal cell growth and maturation. Mutation of the ras gene, causing an amino acid alteration at one of three critical positions in the protein product, results in conversion to a form which is implicated in tumor formation. A gene having such a mutation is said to be "mutant" or "activated." Unmutated ras is called "wild-type" or "normal" ras. It is thought that such a point mutation leading to ras activation can be induced by carcinogens or other environmental factors. Over 90% of pancreatic adenocarcinomas, about 50% of adenomas and adenocarcinomas of the colon, about 50% of adenocarcinomas of the lung and carcinomas of the thyroid, and a large fraction of haematological malignancies such as acute myeloid leukemia, lymphomas and myelodysplastic syndrome have been found to contain activated ras oncogenes. Overall, some 10 to 20% of human tumors have a mutation in one of the three ras genes (H-ras, Ki-ras, or N-ras).

Another example of a gene which is highly involved in the development of cancer is the TP53 gene. It is altered by mutations and/or deletions in more than half of all human cancers. The point mutations are scattered over more than 250 codons and mostly occur as missense mutations. In this respect, the TP53 gene differs from other tumor suppressor genes such as the retinoblastoma tumor suppressor gene (Rb1) and the p16 gene which are most frequently inactivated by deletions or nonsense mutations.

Most malignant tumors show alterations in both alleles of the TP53 gene. This usually involves the complete deletion of one allele and inactivation of the other allele by missense mutations. The result is either a complete lack of TP53 protein or expression of an altered protein. The missense mutations in the highly conserved regions of TP53 have also been associated with increased level of TP53 protein. This seems to result from mutation induced conformational changes, which stabilize the protein and extends its half-life from 4 to 8 hours. The majority of missense mutations cluster in the four highly conserved domains in the central core of the protein. This region is responsible for the sequence specific DNA binding and is therefore of critical importance for the functional integrity of TP53. Seven mutational hot spots have been identified within these domains. These are located at amino acid residues 175, 213, 245, 248, 249, 273, and 282.

Third, infectious diseases are caused by parasites, microorganisms and viruses all of which have their own nucleic acids. The presence of these organisms in a sample of biological material is often determined by a number of traditional methods (e.g., culture). Each organism has its own unique genome and if there are genes or sequences of nucleic acids that are specific to a single species (to several related species, to a genus or to a higher level of relationship), this sequence will provide a "fingerprint" for that organism (or species, etc.), e.g. in the gene of the reverse transcriptase of the HIV virus (A→T mutation in codon 215: Science (1989) 246:1155–1158). Examples of other viruses include HPV, EBV, HSV, Hepatitis B and C and CMV. Examples of micro-organisms include bacteria and more particularly include various strains of mycoplasma, legionella, myco-bacteria, chlamydia, candida, gonocci, shigella and salmonella. As information on the genomes from more organisms are obtained by the scientific community the repertoire of micro-organisms that can be identified by the present invention will increase. In the nucleic acids of some bacterial strains, a particularly great similarity is found in the sequence of their ribosomal genes and their rRNA.

Current attempts in the field of examining samples for different nucleotide sequences focus on the use of only one single difference in the sequence of nucleotides in order to be able to discriminate between nucleic acids. Such differences may be a consequence of e.g. nucleotide exchanges caused by point mutation or in the case of micro-organisms a consequence of inter-species differences. Natural examples of such closely related nucleic acids are alleles, i.e. alternative variants of sequences of a given gene on a defined site on a chromosome.

In each example set forth above one can isolate nucleic acids from a sample and determine if the sample contains any of the above mentioned sequences, i.e. sequences specific for "genetic disease", cancer, infectious diseases or infectious organisms, by identifying one or more sequences that are specific for a diseases or organism. A difficulty when identifying these differences or changes in the nucleotide sequence is however that the detection is not readily applicable in those instances where the number of copies of the target sequence present in a sample is low. In such instances it is difficult to distinguish signal from noise. One way around this problem is to increase the signal. Accordingly, a number of methods have been described to amplify the target sequences present in a sample. One of the best known and widely used amplification methods is the polymerase chain reaction (referred to as PCR) which is described in detail in U.S. Pat. Nos. 4,683,195, 4,683,202 and 4,800,159.

Based upon the PCR technique a number of methods for detection of sequence variations have been described. From Oncogene Research 1 (1989), 235–241 and Nucl. Acids Res. 17 (1989), 8093–8099 a method is known where the area which presumably contains the allelic variant is first amplified in a PCR using specially designed primers and is then treated with a restriction enzyme. The alleles can then be diagnosed once they have been analyzed with restriction fragment length polymorphisms (RFLP). Electrophoretic separation of the cleavage products according to size then reveals whether the corresponding allele was or was not contained in the probe. The disadvantage of this procedure is that it requires specific restrictive digestion. Apart from the fact that this is a cumbersome procedure for each mutation that does not already produce an RFLP it is necessary that a primer can be designed to be adjacent to the point mutation which should allow digestion with a restriction enzyme that cleaves exactly at the given site. This may be difficult due to the reasons listed in said publications.

EP-A-0 332 435 and U.S. Pat. No. 5,605,794 describe a method for selectively detecting a nucleic acid which differs from an adjacent nucleic acid by only one nucleotide. The effect employed here is the following one: from the oligonucleotides which are hybridized to the nucleic acid to be detected only those can be theoretically extended by means of enzymes where the one nucleotide, which is terminal in direction of extension, is complementary to the corresponding nucleotide of the nucleic acid (of the one allele) to be detected. The oligonucleotide is hence selected such that it is only complementary to the nucleic acid to be tested. Thus, the oligonucleotide hybridized to the other allele is theoretically not extended. It turned out, however, that in practice the oligonucleotide hybridized to the other allele is, though only to a minor extent, also extended. This reduces the sensitivity and, particularly, the specificity of the method. Non-specific extension may easily occur especially when T is part of the 3'-terminal mismatch or when the mismatch is a C:A mismatch (Kwok et al. (1990). Nucleic Acids Research, 18:999–1005). In order to increase specificity, EP-A-0 332 435 proposes to select the nucleotide sequence of an oligonucleotide such that the terminal area contains another nucleotide that is not complementary to the corresponding nucleotide of the two nucleic acids. For the detection of both alleles two reactions must be carried out with only one of two alleles being detected per reaction. This procedure requires the synthesis of two allele-specific primers and one complementary strand primer. The sample is amplified in two reactions: once in a PCR with the primer of the complementary strand and one of the allele-specific primers, and in the second parallel reaction, a PCR, it is amplified with the complementary strand primer and the second allele-specific primer. If the suspected allele-specific PCR product is not detected in one of the reactions, it is assumed that the respective allele is not present in the sample. Since homozygous DNA-samples contain only one of the two alleles which can be detected in only one of the two reactions, it is necessary to use two additional primers which produce the same control product in all reactions. This control product is different from the specific product in order to control the efficiency of the respective PCR of the other allele and to establish the absence of the respective allele. If a control product is present in the PCR product but no specific product of the allele is found, the sample is not likely to contain the allele tested for in the reaction. In this method, the presence or absence of two alleles must be established in two separate reactions and each individual PCR must comprise a control PCR.

Biochem. Biophys. Res. Commun. (1989), 160:441–447 proposes to increase the selectivity by decreasing the dNTP concentration. Even if this additional measure is taken, the detection of alleles in separate batches can yield non-specific products.

In a ligase chain reaction (WO 89/09835), thermostable ligase is used to specifically link two adjacent oligonucleotides. This occurs only if they are hybridized to a complementary target at a stringent hybridization temperature and if base-pairing at the site of linkage is complete. If two alleles differ from each other as a consequence of a mutation at the linkage site, the above condition of complete base-pairing is fulfilled for only one of the alleles. Two additional oligonucleotides, which are complementary to the first two, are then necessary to amplify the ligation product in the ligase chain reaction. To date, the detection of two alleles requires two reactions with at least six oligonucleotides, and the amplification product is detected with a radioactive label (Proc. Natl. Acad. Sci. U.S.A. (1991), 88:189–193).

From Proc. Natl. Acad. Sci. U.S.A. (1985), 82:1585–1588 and from New England Journal of Medicine (1987), 317:985 a method of detecting alleles is known which is based upon differential hybridization of "allele-specific" oligonucleotides (ASO) with the alleles under examination. Two oligonucleotides, each 20 bp in length, for example, are synthesized. Each matches one of the two different alleles but has a mismatch to the other allele located in the middle of the oligonucleotide sequence. Discrimination between alleles is then possible by differential hybridization with labelled oligonucleotides. This applies to the analysis of both human genomic DNA and PCR products. Direct and discrete analysis of genomic DNA is also possible with this method but requires additional digestion and electrophoresis.

Nucleic Acids Research (1989), 17:2437–2448 and EP-A-0 333 465 describe a method of testing pre-amplified human genomic DNA for the presence of various alleles in a few additional PCR cycles by competition of allele-specific primers (competitive oligonucleotide priming= COP). The above described ASO-technique is then converted into a PCR technique. In the original ASO-technique, an error rate of 5% caused by cross hybridization is acceptable since a comparison of the signal intensities during corresponding controls allows an unequivocal interpretation of the results. In a PCR reaction, however, where the primers are allele-specific oligonucleotides, the error rate for a sample that contains only one of the alleles would after ten cycles amount to 12% if this error occurred in a reagent mixture where both alleles are amplified. It could indeed be demonstrated that primer competition increased selectivity, however, the area of interest of the genomic DNA was first amplified in a PCR and the analysis for the different alleles was then carried out in ten subsequent cycles. Two allele-specific primers and a complementary strand primer were used in these cycles and in two reactions one of the allele-specific primers was radioactively labelled. A selective detection of different alleles has been demonstrated for oligonucleotides of 12 to 16 bases in length whereas longer oligonucleotides under the given conditions also yielded non-specific products.

There is a need for a simple and still very specific method for directly detecting at least one single base difference in a sample containing nucleic acids such as genomic DNA in which detection steps are minimized resulting in a method which may be performed quickly, accurately and easily with minimal operator skills.

Methods that are based on differential hybridization can only be applied in certain situations and are moreover very complex and susceptible to interference. Also, pre-amplification is a procedural step, e.g. during COP, which preferably is eliminated.

All of the above mentioned methods for detecting variant nucleic acids have the same feature of relying on unmodified nucleotides as the discriminating factor in the detection of the variant nucleic acids.

SUMMARY OF THE INVENTION

The present invention provides a simple method for the specific detection of variant nucleic acids which does not require digestion by restriction enzymes, allows amplifying the nucleic acids in one reagent mixture and does not depend on subsequent enzymatic reactions. A crucial component in the invention is LNA which is a novel class of DNA analogues that possess some extraordinary features that make it a prime candidate for improving in vitro DNA diagnostics. The LNA monomers are bi-cyclic compounds structurally very similar to RNA-monomers, see formula I. LNA share most of the chemical properties of DNA and RNA, it is water-soluble, can be separated by gel electrophoreses, ethanol precipitated etc (Tetrahedron, 54, 3607–3630 (1998)). However, introduction of LNA monomers into either DNA or RNA oligos results in unprecedented high thermal stability of duplexes with complementary DNA or RNA, while, at the same time obeying the Watson-Crick base-pairing rules. This high thermal stability of the duplexes formed with LNA oligomers together with the finding that primers containing 3' located LNA(s) are substrates for enzymatic extensions, e.g. the PCR reaction, is used in the present invention to significantly increase the specificity of detection of variant nucleic acids in the in vitro assays described in the application. The amplification processes of individual alleles occur highly discriminative (cross reactions are not visible) and several reactions may take place in the same vessel.

DETAILED DESCRIPTION OF THE INVENTION

The present invention relates to a method of detecting variant nucleic acids having nucleotide sequences which differ from one another in at least one position A. The method comprises at least two steps:
  a) Performing an extension reaction with at least one diagnostic oligonucleotide as a primer for the extension reaction, the at least one diagnostic oligonucleotide being a LNA-containing oligonucleotide wherein the LNA(s) is/are preferably found at position A or at neighbouring positions to position A, most preferably at the 3'-end of the oligonucleotide,
  b) detecting the extension product, e.g. by standard gel electrophoresis, capillary electrophoresis or various hybridizations assays.

Other embodiments of the invention are further extension and amplification using the at least one oligonucleotide, a set of oligonucleotides, different sets of oligonucleotides, a reagent kit and various applications and uses of said method.

The "target nucleic acids" in accordance with the invention are nucleic acids that may be contained in a sample and the presence of which is of interest, the nucleotide sequences of the target nucleic acids (Q' and Q) are substantially identical, but the nucleic acid Q' differs in at least one position of its nucleotide sequence from the nucleotide sequence of nucleic acid Q. The position of the difference in the nucleotide sequence is referred to as "position A". Position A is also referred to as a polymorphous site and the presence of a position A in a nucleic acid is referred to as a gene polymorphism. If the variant nucleotide sequences comprise several different nucleic acids ($Q'_1, Q'_2, \ldots Q'_e$) the positions of differences will be referred to as $A_1, A_2, \ldots A_e$. Such differences may occur, for example, as a consequence of point mutations or may be caused by deletions or insertions of one or several bases. The nucleic acids to be detected can be RNA or DNA and especially in the diagnosis of bacteria rRNA has proven to be particularly suitable.

The term "diagnostic oligonucleotide" refers to an oligonucleotide, which at position A has a nucleotide that is complementary to the nucleotide found at position A of the target nucleic acid to be detected and which is capable of discriminating between different target nucleic acid sequences ($Q, Q'_1, Q'_2, \ldots Q'_e$) under the hybridization conditions given and only initiate extension of the target nucleic acid sequences which contain at a position A a nucleotide which is complementary to the nucleotide at position A of the diagnostic oligonucleotide.

The term "product target" refers to those nucleotides that are extension products of the original target nucleic acids. Product targets can also be used as target nucleic acids and are usually smaller than the original target.

The term "position" refers to a defined site on the nucleic acid. Such a position may, for example, be occupied by a nucleotide.

The term "allele" refers to any of the forms of the same gene that occur at the same locus on a homologous chromosome but differ in base sequence.

Nucleotides are referred to as being complementary if regular Watson-Crick base-pairing is ensured (e.g. G-C, A-T or A-U). This complementary base-pairing leads to matches whereas non-complementary base-pairing leads to mismatches. Any nucleobase creating such base-pairing (e.g. 7-deaza-dGTP, dITP, LNA-base analogues etc.) is also referred to as being complementary.

For the realization of the method of the invention, the nucleic acids to be detected must be present in a form that is suitable for in vitro reaction. The sample to be examined, e.g. tissue sample, tissue extract, individual cells or a cell-containing fluid, is digested in a known manner in order to break down the cell walls (e.g. thermal, enzymatic or chemical lysis or combinations thereof to release the nucleic acids.

The sample is then brought into contact with diagnostic oligonucleotides of the invention. The conditions selected are such that the oligonucleotides of the invention hybridize with the corresponding areas of the nucleic acids to be detected. This hybridization is generally known as annealing. Hybridization with irrelevant nucleic acids, i.e. those not to be detected, is avoided by selecting a suitable nucleotide sequence, length of the nucleotide, hybridisation temperature, adjuvants etc. (see Ausubel et. al in Current Protocols in Molecular Biology, pub. John Wiley & Sons (1998) and the details in the examples).

The number of different diagnostic oligonucleotides of the invention corresponds to at least the number of different target nucleic acids to be detected. The detection of two different mutations hence requires at least two different diagnostic oligonucleotides, each containing a nucleotide which is complementary to only one of the nucleotides which may be present at the A position of the target nucleic acid. The diagnostic oligonucleotides used have a preferred length of less than 50 nucleotides, preferably in the range from 5 to 40 nucleotides, more preferably in the range from 5 to 30 nucleotides, even more preferably in the range from 5 to 25 nucleotides, e.g. 6, 7, 8, 9, 10, 11, 12, 13, 14, 15, 16, 17, 18, 19, 20, 21, 22, 23, 24 or 25. Each of the diagnostic oligonucleotides has a nucleotide sequence which is so highly complementary with respect to the area contiguous to position A that this oligonucleotide can hybridize with the nucleic acid to be detected.

The methods of the invention are improvements over the processes that are based on the principle of competitive priming or of the mismatch-priming-method and related methods. However, regardless of the variant method applied, each diagnostic oligonucleotide used in the detection of a target nucleic acid comprises at least one LNA. This LNA preferably corresponds to and is complementary to the nucleotide found at position A of the target nucleic acid to be detected.

One embodiment of the invention is a method for detecting in a sample the presence of a target nucleic acid Q' whose nucleotide sequence differs from a nucleic acid Q in at least one position A, the method comprising the steps of a) combining nucleic acids present in the sample with an appropriate amount of nucleoside triphosphates, an agent for polymerisation of the nucleoside triphosphates and at least one diagnostic oligonucleotide containing at position A a nucleotide which is capable of hybridizing to the nucleotide at position A of nucleic acid Q' but not to a nucleotide at position A of nucleic acid Q under hybridisation conditions, the at least one diagnostic oligonucleotide containing at least one LNA, b) extending any oligonucleotides which hybridize to the nucleic acids present in the sample to form extension products, wherein said nucleic acids are used as templates, c) detecting any nucleic acids formed in step b) and thereby the presence of nucleic acid Q' in the sample.

This method can e.g. be applied to the reverse transcription of RNA into cDNA and other first strand synthesis applications. The method can further be made more efficient by cycling the extension reaction by the addition of following steps instead of step c)

$c_1$) after the formation of extension products treating the reaction mixture under denaturing conditions to separate the extension products from the template, $d_1$) hybridising in the presence of an appropriate amount of nucleoside triphosphates and an agent for polymerisation of the nucleoside triphosphates the single stranded nucleic acids of step $c_1$) with at least one diagnostic oligonucleotide containing at position A a nucleotide which is capable of hybridizing to the nucleotide at position A of nucleic acid Q' but not to a nucleotide at position A of nucleic acid Q under hybridisation conditions, the at least one diagnostic oligonucleotide containing at least one LNA, $e_1$) repeating steps $c_1$) through $d_1$) a sufficient number of times to result in a detectable amount of extension products, $f_1$) detecting the extension products formed.

This method will result in a linear amplification and can further be extended to include re-amplification steps including a "downstream oligonucleotide" acting as primer for the synthesis of extension products of the opposite strand in the target nucleic acid which allows for an PCR-type of exponential amplification. The method for detecting the presence of a target nucleic acid Q' whose nucleotide sequence differs from a nucleic acid Q in at least one position A in a sample, will then comprise the steps of a) combining the nucleic acids with an appropriate amount of nucleoside triphosphates, an agent for polymerisation of the nucleoside triphosphates, at least one downstream oligonucleotide and at least one diagnostic oligonucleotide containing at position A a nucleotide which is capable of hybridizing to the nucleotide at position A of nucleic acid Q' but not to a nucleotide at position A of nucleic acid Q under hybridisation conditions, the at least one diagnostic oligonucleotide containing at least one LNA, b) extending any oligonucleotides which hybridize to the nucleic acids to form extension products, wherein said nucleic acids are used as templates, c) after the formation of extension products treating the reaction mixture under denaturing conditions to separate the extension products from the template, d) hybridising in the presence of an appropriate amount of nucleoside triphosphates and an agent for polymerisation of the nucleoside triphosphates the single stranded nucleic acids from step c) with at least one downstream oligonucleotide and at least one diagnostic oligonucleotide containing at position A a nucleotide which is capable of hybridizing to the nucleotide at position A of nucleic acid Q' but not to a nucleotide at position A of nucleic acid Q under hybridisation conditions, the at least one diagnostic oligonucleotide containing at least one LNA, e) repeating steps c) through d) a sufficient number of times to result in a detectable amount of extension products, f) detecting the extension products formed.

Depending on which variant of the method in accordance with the invention is selected, the LNA-nucleotide(s) is/are located at a given site of the diagnostic oligonucleotides, preferably at position A, for example at internal positions of the diagnostic oligonucleotide or, preferably, at the 3'-end of the diagnostic oligonucleotides.

The presently described invention is particularly suited for multiplex analyses. In a number of situations genes are analysed which may contain a number of different mutations at different sites e.g. the TP53 gene having mutations in numerous codons. By including a number of carefully matched LNA-oligo/DNA-oligo pairs, each of which is directed towards a particular mutation and each of which may result in a characteristically sized fragment or characteristically labelled fragment, it is possible to discriminate between a number of different mutations by size-fractionating the fragments produced or detecting the labels of the fragments. The method for detecting target nucleic acids whose nucleotide sequences differ from one another in at least one position A in this case is similar to the above mentioned but here the diagnostic oligonucleotides consist of more than one sequence, the method thus comprises the steps of a) combining the nucleic acids with an appropriate amount of nucleoside triphosphates, an agent for polymerisation of the nucleoside triphosphates and at least one set of diagnostic oligonucleotides under hybridisation conditions, the at least one set of diagnostic oligonucleotides having nucleotide sequences which differ from one another in at least one position A and contain at least one LNA, b) extending any oligonucleotides which hybridize to the nucleic acids to form extension products, wherein said nucleic acids are used as templates, c) detecting the nucleic acids formed in step b).

This constitutes a method which e.g. can be used as a sequence specific first strand synthesis of different nucleic acid sequences and can e.g. be used as a sequence specific reverse transcription of RNA. As also described above the method for detecting target nucleic acids whose nucleotide sequences differ from one another in at least one position A can be rendered more efficient by repeating the extension reaction a number of times as can be described by the addition of following steps instead of step c)

$c_1$) after the formation of extension products treating the reaction mixture under denaturing conditions to separate the extension products from the template, $d_1$) hybridising in the presence of an appropriate amount of nucleoside triphosphates and an agent for polymerisation of the nucleoside triphosphates the single stranded nucleic acids from step $c_1$) with at least one set of diagnostic oligonucleotides whose nucleotide sequences differ from one another in at least one position A to synthesise further extension products, $e_1$) repeating steps $c_1$) through $d_1$) a sufficient number of times to result in a detectable amount of extension products, $f_1$) detecting the extension products formed.

This method will result in a linear amplification of the different nucleic acids corresponding to the used oligonucleotides and can further be extended to include re-amplification steps including one or more downstream oligonucleotides acting as primers for the synthesis of the opposite strand in the target nucleic acid which allows for an PCR-type of exponential amplification. The method for detecting target nucleic acids whose nucleotide sequences differ from one another in at least one position A, will then comprise the steps of a) combining the nucleic acids with an appropriate amount of nucleoside triphosphates, an agent for polymerisation of the nucleoside triphosphates, at least one downstream oligonucleotide and at least one set of diagnostic oligonucleotides under hybridisation conditions, the at least one set of diagnostic oligonucleotides having nucleotide sequences which differ from one another in at least one position A and contain at least one LNA, b) extending any oligonucleotides which hybridize to the nucleic acids to form extension products, wherein said nucleic acids are used as templates, c) after the formation of extension products treating the reaction mixture under denaturing conditions to separate the extension products from the template, d) hybridising in the presence of an appropriate amount of nucleoside triphosphates and an agent for polymerisation of the nucleoside triphosphates the single stranded nucleic acids step c) with at least one downstream oligonucleotide and at least one set of diagnostic oligonucleotides being oligonucleotides whose nucleotide sequences differ from one another in at least one position A to synthesise further extension products, e) repeating steps c) through d) a sufficient number of times to result in a detectable amount of extension products, f) detecting the extension products formed.

Also in these variants of the method it is preferred that the preferably 3'-terminal LNA-nucleotide of the diagnostic oligonucleotides corresponds to the position of the mutation (position A of the target nucleic acid) since the hybridization has a higher selectivity and specificity under these conditions.

It is preferred that the agent for polymerization in all the above mentioned methods is an enzyme e.g. a RNA polymerase, a revers transcriptase or a DNA polymerase. The DNA polymerase is preferably a thermostable DNA polymerase, e.g. Taq, Pfu, Pwo or Tth.

The principle of the detection of variant nucleic acids can be illustrated with the following example. One single reaction vessel contains a reagent mixture for a PCR for the simultaneous detection of two alleles of one gene. These alleles differ in one base position (position A of allele Q' (mutant) and position A of allele Q (normal)). Three primers, one generic primer complementary to a sequence found in both alleles and two primers each selective for only one of the two alleles, are used in the reaction. Primer selectivity is effected in that the base at the 3'-end of the one selective primer is complementary to position A of Q', the base of the other primer is complementary to position A of Q. Both primers contain a LNA at the 3'-position corresponding to position A. Moreover, in order to distinguish easily between the resulting PCR products, it is possible, for example to select the allele-specific primers such that PCR products of different lengths or with different labels are produced and conveniently detected by e.g. gel electrophoresis, capillary electrophoresis or various hybridizations techniques know in the art.

The sensitivity of the hybridization towards detection of differences in nucleotide sequence at a single-base may be enhanced through use of a ligase reaction. The observation in general (Nature 327, 293–297 (1987) and Nature 327, 298–303 (1987)) is that the shorter the length of a given oligonucleotide the better the discrimination towards single-base differences. However, short DNA-oligos have very low $T_m$ thus setting a lower limit to the length of DNA-oligos. On the other hand, the LNA-modification results in a very significant increase in the $T_m$ (3–8° C. pr. modification), therefore even short primers of 4–25 nucleotides are able to hybridise to a target nucleic acid at conditions compatible with standard PCR and LCR (Ligase Chain Reaction) conditions and furthermore do so with an improved discrimination towards single base differences. LCR, like PCR, uses multiple cycles of alternating temperature to amplify the numbers of a targeted sequence of DNA. LCR, however, does not use individual nucleotides for template extension but instead relies upon an excess of oligonucleotides which are complementary to both strands of the target region. Following the denaturation of a double stranded template DNA, the LCR procedure begins with the ligation of two (or more) oligonucleotide primers complementary to adjacent regions on one of the target strands. Oligonucleotides complementary to either strand can be joined. After ligation and a second denaturation step, the original template strands and the two (or more) newly joined products serve as templates for additional ligation to provide an exponential amplification of the targeted sequences. This method has been detailed in Genomics, 4:560–569 (1989), which is incorporated herein by reference. In the present invention it is proposed to include one short oligonucleotide containing at least one LNA preferably containing between 4 and 25 nucleotides, more preferably between 5 and 20 nucleotides, even more preferably between 6 and 15 nucleotides, e.g. 6, 7, 8, 9, 10, 11, 12, 13,14, 15 nucleotides. This oligonucleotide is directed against gene-polymorphisms in the "LCR"-procedure. After multiple cycles of alternating temperature the numbers of a targeted sequence has been amplified and can be detected by gel electrophoresis, "sandwich"-hybridisation, or any of the many methods mentioned in the art. This is described by the following steps a) combining the target nucleic acids with an appropriate amount of nucleoside triphosphates, at least two oligonucleotides wherein at least one of said oligonucleotides is a diagnostic oligonucleotide and an agent for ligation of the oligonucleotides under hybridisation conditions, the at least one diagnostic oligonucleotide being an oligonucleotide containing at position A a nucleotide which is complementary to the nucleotide found at position A of the target nucleic acid to be detected, said diagnostic oligonucleotide contains at least one LNA, b) ligating any oligonucleotides which hybridize to the nucleic acids at adjacent positions to form ligation products, wherein said nucleic acids are used as templates, c) treating the reaction mixture under denaturing conditions to separate the ligation products from the template after the ligation, d) hybridising in the presence of an appropriate amount of nucleoside triphosphates and an agent for ligation of the oligonucleotides under hybridisation conditions the single stranded nucleic acids from step c) with at least one oligonucleotide being complementary to the ligation product from step b) and at least one diagnostic oligonucleotide being an oligonucleotide containing at position A a nucleotide which is complementary to the nucleotide found at position A of the target nucleic acid to be detected, said diagnostic oligonucleotide contains at least one LNA, e) repeating steps c) through d) a sufficient number of times to result in a detectable amount of ligation products, f) detecting the ligation products formed.

The method can of course be stopped after step b) and visualized immediately.

The preferred agent for ligation is an enzyme, e.g. a ligase, preferably a DNA-ligase, e.g. T4-DNA ligase, more preferably a thermostable ligase, e.g. Taq DNA ligase.

Another improvement of existing methods relates to the combined use of LCR and PCR. Accordingly it is proposed to hybridize two (or more) short (e.g. 8 bp) upstream LNA-primers to the template instead of one upstream primer. When two (or more) short LNA-primers are hybridizing next to each other they can be joined into one by a ligation reaction. Thus the ligation will ensure sufficient specificity. Following the ligation the ligated primers can be extended. Since both thermostable ligase and polymerases have been described it is suggested to use multiple cycles of alternating temperature to amplify the numbers of a targeted sequence of DNA. Following the denaturation of a double stranded template DNA, the procedure begins with the ligation of two (or more) oligonucleotide primers complementary to adjacent regions on one of the target strands. The joined/ligated oligonucleotides form one upstream "primer" which is extended by the polymerase. After a second denaturation step, the original template strands and the newly formed products serve as templates for additional ligation and extension to provide an exponential amplification of the targeted sequences. After multiple cycles of alternating temperature the numbers of a targeted sequence has been amplified.

The diagnostic oligonucleotides of all the above mentioned methods have the general formula of $$5'-Nu_a(Nu_bLNA_c)_mNu_dA_eNu_f-3' \qquad a)$$

where A is a LNA in position A in which the variant nucleic acid sequences of the target nucleic acids differs from one another; LNA is a LNA; Nu is a monomer selected from the group consisting of any nucleotides other than LNA capable of forming specific base-pairs with the variant nucleic acids; a, b, c, d and f are integers between 0 and 30, m is an integer between 1 and 8 and e is an integer between 1 and 6 with the proviso that the sum of a, b, c, d, e and f is at least 5.

This means that it is preferred that at least one position A of the diagnostic oligonucleotide sequence is complementary to position A of the target nucleic acid sequence to be detected but not to position A of the other target nucleic acid sequences. Furthermore, it is preferred that at least one position A in the diagnostic oligonucleotide is a LNA.

The specific detection of the extension products, which is a measure for the presence or the quantity of the nucleic acid to be detected in the sample is, for example, also possible by making use of the fact that the oligonucleotides used are discriminated by one additional feature. Such a distinction could be, for example, the varying lengths of oligonucleotides of one set. The extension of the different diagnostic oligonucleotides then produces extension products of different length. The diagnostic oligonucleotides can also be distinguished by having different labels. Such labels are, for example, colour or fluorescence molecules or chemical groups which can be detected in a subsequent reaction with the aid of a detectable group. Chemical groups of this kind include, e.g. haptens such as digoxin and digoxigenin. Haptens can be detected by reacting them with a labelled antibody to the hapten, the label is then detected. Another hapten could be biotin, for example, which can be detected by using a differently labelled antibody or straptavidin.

In the present context, the term "label" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radioisotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy), enzymes (such as peroxidases, alkaline phosphatases, β-galactosidases, and glycose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, Ruthenium, Europium, Cy5, Cy3, etc.

The various extension products which are a measure for the quantity and the presence of the nucleic acid to be detected can be detected in various ways. They can be separately detected after separating the reagent mixture or sequentially once the reagent mixture is obtained or, provided appropriate labels are used, simultaneously according to known methods. Preferably the individual oligonucleotides in each oligonucleotide set is labelled with detectable groups, said detectable groups being different for each individual diagnostic oligonucleotide.

The method described in EP-A-0 324 474 has proved to be the preferred method for the use of steroid hormones as markers. Another method is the use of different fluorescent dyes. The oligonucleotides can either be labelled directly or antibodies to chemical groups can, for example, be provided with corresponding fluorescent labels. The various allelic products can be detected by simultaneously measuring the fluorescence in several channels corresponding to the number of different oligonucleotide primers. Also, part of the products can be labelled with fluorescent labels whereas enzymes can be used for other products from the same reagent mixture. In principle it is possible to employ any known method of labelling and detecting.

In a sequential or simultaneous detection, the two different chemical groups, preferably haptens which are detected by different antibodies, can be used, for example, to label the two oligonucleotides. Such haptens include digoxigenin, biotin, and fluorescein. Preferably, the antibody to fluorescein and the antibody to digoxigenin then have different enzymes as labels. The nucleic acids are then detected by sequential or simultaneous contact with enzyme-specific detectable substrates.

The mixture of the common extension reaction could also be subject to a denaturing reaction consequently using a capture probe to bind the single-stranded extension products to a solid phase which is immobilized or can be immobilized via a group (e.g. biotin). Alternatively, the capture probe could be permanently bound to a solid phase in advance e.g. by anthraquinone photochemistry (WO 96/31557). In these procedures, the extension products of the reaction are immobilized together with all nucleic acids to be detected. Due to the specificity of the capture probe the nucleic acids can be detected sequentially (separated by a washing step). If the signal to be detected can be produced and detected at the same time in one vessel, such a washing step can be omitted.

In a variant two (or correspondingly more if detection involves more than two allels and if more than two sets of specific primers are used) sufficient aliquots of liquid are taken from the reagent mixture after the extension reaction has occurred, and each aliquot is tested for extension products. The aliquots are taken from a multiplex reaction, and depending on the number of different labels used for the oligonucleotides, a corresponding number of amplification products can be detected in each aliquot.

The method of the invention can be employed in a variety of applications. It is possible, for example, that the target nucleic acids to be detected from one single test subject (individual diagnostics) are related to certain diseases, e.g. metabolic disorders, life style diseases, cancer or inheritable diseases. Examples of life style diseases are obesity, familial hypercholesterolaemia, atherosclerosis and diabetes.

The sample containing the nucleic acid to be detected will typically be cells, a tissue sample or a tissue extract of either archae, prokaryotic or eukaryotic origin. In the case the sample originates from an animal, e.g. a mammal or a human, the sample can be blood, serum, plasma, reticulocytes, lymphocytes, urine, bone marrow tissue, cerebrospinal fluid or any product prepared from blood or lymph or any type of tissue biopsy e.g. a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammae biopsy, an uterus biopsy, a testicular biopsy, an eye biopsy or a brain biopsy.

Moreover, because of its good specificity, the method is also suited for assays where probes are subject to pool-screening. According to this principle a great number of individual probes of different test subjects are mixed. When diagnosing the defect in the apo B 3500-gene, e.g. in connection with diabetes, familial hypercholesterolaemia, atherosclerosis or obesity, it has proven to be suitable to combine 64 probes in one pool. With the method of the invention it is possible to determine the presence or absence of this defect in a probe contained in the pool. When several partial pools from a pool with positive results are successively tested several times in accordance with the method of the invention, a small (as compared to prior art) number of determinations suffices to detect the gene which bears the defect.

In the method of the invention it has proven to be particularly advantageous to simultaneously detect the gene that does not bear the defect provided this gene is present. When screening a pool, it is possible to alternatively detect the mutant product or, if no mutant allele is present, to detect the normal product. In addition to its function as a control for the reaction as such, the detection of both alleles is also a means of quantifying the nucleic acids to be detected.

Since the samples used in pool-screening methods are not patient-specific but anonymous, these methods can be used in the testing of diseases which are of particular epidemiological relevance, e.g. the contamination rate of the AIDS Virus or, e.g. the frequency of elevated cholesterol levels, hypertension or diabetes (mass screening). These methods serve to determine the frequency of alleles.

The same applies to the detection or diagnostics of particular species, sub-species or strains of organisms, micro-organisms or particular species, sub-species or strains of infectious agents especially of bacteria and in some cases to virus. The area of particular interest focus on the simultaneous detection of closely related pathogenic/non-pathogenic species or strains. Further, the method of the invention is also suited to reliably detect e.g. *E. coli* K12 (evaluated in accordance with law of gene technology) via the known AT-sequences whereby various strands of *E. coli* are distinguished. The method can hence also be applied in analysis of environmental conditions.

An important subject matter of the invention is the use of diagnostic oligonucleotides containing at least one LNA covalently attached to a solid surface e.g. by anthraquinone photochemistry (WO 96/31557) in e.g. an array format (Nature Genetics, suppl. vol. 21, Jan 1999, 1–60). Different diagnostic oligonucleotides containing at least one LNA directed against different target nucleic acid sequences can be spotted in the array and permanently affixed to the solid surface. Such an array can subsequently be subjected to an extension reaction or to PCR. If the diagnostic oligonucleotides are attached to a suitable microscopically slide, e.g. surface-treated glass or polycarbonate slide, the extension reaction or the PCR reaction can be performed in one of the commercially available in situ PCR thermocyclers. After PCR the positive spots (indicative of a specific mutation) can be detected by a suitable label. The result of such a procedure would be a semi-quantitative assessment of a large number of different target nucleic acids.

The main advantage of the invention over prior art is the possibility of simultaneously detecting allelic compounds in mixtures contained in one single vessel with practically no relevant secondary reactions. Digestions with restriction enzymes or subsequent hybridization is not required. This object is achieved by virtue of the fact that LNA oligomers obey the Watson-Crick base-pairing rules and form duplexes that are significantly more stable than similar duplexes formed by DNA:DNA, and that primers containing 3' located LNA(s) are substrate for the PCR reaction. The amplification processes of the individual alleles occur highly discriminative (cross reactions are not visible) and several reactions may take place in the same vessel.

Another subject matter of the invention is a reagent kit for the detection of nucleic acids. Said kit comprises a set of oligonucleotidep in accordance with the invention and, if necessary, additional oligonucleotides and adjuvants necessary for the extension of the oligonucleotides. Further, the reagent kit can comprise additional oligonucleotides, for example, complementary strand primers. Preferably, the kit provides the enzyme and the oligonucleotides and the other reagents in separate containers.

When used herein, the term "LNA" or "LNA-containing oligonucleotide" refer to oligomers comprising at least one nucleoside analogue of the general formula I

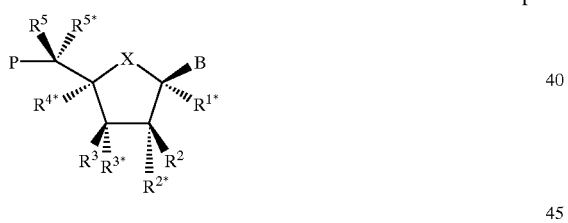

I wherein

X is selected from —O—, —S—, N(R$^{N*}$)—, —CR$^6$(R$^{6*}$)—;

B is selected from nucleobases;

P designates the radical position for an internucleoside linkage to a succeeding monomer, or a 5'-terminal group, such internucleoside linkage or 5'-terminal group optionally including the substituent R$^5$;

R$^3$ or R$^{3*}$ is P* which designates an internucleoside linkage to a preceding monomer, or a 3'-terminal group;

R$^{4*}$ and R$^{2*}$ together designates a biradical consisting of 1–4 groups/atoms selected from —C(R$^a$R$^b$)—, —C(R$^a$)=C(R$^a$)—, —C(R$^a$)=N—, —O—, —Si(R$^a$)$_2$—, —S—, —SO$_2$—, —N(R$^a$)—, and >C=Z, wherein Z is selected from —O—, —S—, and —N(R$^a$)—, and R$^a$ and R$^b$ each is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkenyloxy, carboxy, C$_{1-12}$-alkoxycarbonyl, C$_{1-12}$-alkylcarbonyl, formyl, aryl, aryloxycarbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted, and where two geminal substituents R$^a$ and R$^b$ together may designate optionally substituted methylene (=CH$_2$, optionally substituted one or two times with substituents as defined as optional substituents for aryl); and each of the substituents R$^{1*}$, R$^2$, R$^3$, R$^{3*}$, R$^5$, R$^{5*}$, R$^6$ and R$^{6*}$ which are present and not involved in P or P*, is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present and not involved in a biradical, is selected from hydrogen and C$_{1-4}$-alkyl; and basic salts and acid addition salts thereof.

When used herein, the term "LNA" (Locked Nucleoside Analogues) refers to the bi-cyclic nucleoside analogues incorporated in the oligomer (general formula I).

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-N$^6$-methyladenine, 7-deazaxanthine, 7-deazaguanine, N$^4$,N$^4$-ethanocytosin, N$^6$,N$^6$-ethano-2,6-diaminopurine, 5-methylcytosine, 5-(C$^3$–C$^6$)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

When used herein, the term "DNA intercalator" means a group which can intercalate into a DNA or RNA helix, duplex or triplex. Examples of functional parts of DNA intercalators are acridines, anthracene, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin. Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphtoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alkohols, secondary alkohols, tertiary alkohols, phenols, alkyl halides, thiols, disulphides, primary amines, secondary amines, tertiary amines, hydrazines, epoxides, maleimides, and boronic acid derivatives.

In the present context, the term "chelating group" means a molecule that contains more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alkohols, secondary alkohols, tertiary alkohols, phenols, alkyl halides, thiols, disulphides, primary amines, secondary amines, tertiary amines, hydrazines, epoxides, maleimides, $C_1$–$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, potylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

It will be clear for the person skilled in the art that the above-mentioned specific examples under DNA intercalators, photochemically active groups, thermochemically active groups, chelating groups, reporter groups, and ligands correspond to the "active/functional" part of the groups in question. For the person skilled in the art it is furthermore clear that DNA intercalators, photochemically active groups, thermochemically active groups, chelating groups, reporter groups, and ligands are typically represented in the form M-K- where M is the "active/functional" part of the group in question and where K is a spacer through which the "active/functional" part is attached to the 5- or 6-membered ring. Thus, it should be understood that the group B, in the case where B is selected from DNA intercalators, photochemically active groups, thermochemically active groups, chelating groups, reporter groups, and ligands, has the form M-K-, where M is the "active/functional" part of the DNA intercalator, photochemically active group, thermochemically active group, chelating group, reporter group, and ligand, respectively, and where K is an optional spacer comprising 1–50 atoms, preferably 1–30 atoms, in particular 1–15 atoms, between the 5- or 6-membered ring and the "active/functional" part.

In the present context, the term "spacer" means a thermochemically and photochemically non-active distance-making group and is used to join two or more different moieties of the types defined above. Spacers are selected on the basis of a variety of characteristics including their hydrophobicity, hydrophilicity, molecular flexibility and length (e.g. see Hermanson et. al., "Immobilized Affinity Ligand Techniques", Academic Press, San Diego, Calif. (1992), p. 137-ff). Generally, the length of the spacers are less than or about 400 Å, in some applications preferably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-β-alanine, polyglycine, polylysine, and peptides in general, oligosaccharides, oligo/polyphosphates. Moreover the spacer may consist of combined units thereof. The length of the spacer may vary, taking into consideration the desired or necessary positioning and spatial orientation of the "active/functional" part of the group in question in relation to the 5- or 6-membered ring. In particularly interesting embodiments, the spacer includes a chemically cleavable group. Examples of such chemically cleavable groups include disulphide groups cleavable under reductive conditions, peptide fragments cleavable by peptidases, etc.

In one variant, K designates a single bond so that the "active/functional" part of the group in question is attached directly to the 5- or 6-membered ring.

In a preferred embodiment, the substituent B in the general formulae I and II is preferably selected from nucleobases, in particular from adenine, guanine, thymine, cytosine and urasil.

In the oligomers (formula I), P designates the radical position for an internucleoside linkage to a succeeding monomer, or a 5'-terminal group. The first possibility applies when the LNA in question is not the 5'-terminal "monomer", whereas the latter possibility applies when the LNA in question is the 5'-terminal "monomer". It should be understood (which also will be clear from the definition of internucleoside linkage and 5'-terminal group further below) that such an internucleoside linkage or 5'-terminal group may include the substituent $R^5$ (or equally applicable: the substituent $R^{5*}$) thereby forming a double bond to the group P. (5'-Terminal refers to the position corresponding to the 5' carbon atom of a ribose moiety in a nucleoside.)

On the other hand, an internucleoside linkage to a preceding monomer or a 3'-terminal group (P*) may originate from the positions defined by one of the substituents $R^3$ or $R^{3*}$, preferably from the positions defined by the substituents $R^{3*}$. (3'-Terminal refers to the position corresponding to the 3' carbon atom of a ribose moiety in a nucleoside.)

It should be understood that the orientation of the group P* either as $R^{3*}$ ("normal" configuration) or as $R^3$ (xylo configuration) represent two equally interesting possibilities. It has been found that all-"normal" ($R^{3*}$=P*) oligomers and oligomers with combinations of "normal" LNA monomers and nucleotides (2-deoxynucleotides and/or nucleotides) hybridise strongly (with increasing affinity) to DNA, RNA and other LNA oligomers. It is presently believed that combination of all-xylo LNA oligomers and oligomers with xylo LNA ($R^3$=P*) monomers and, e.g., xylo nucleotides (nucleotides and/or 2-deoxynucleotides) will give rise to comparable hybridisation properties. It has been shown that the an oligomer with "normal" configuration ($R^{3*}$=P*) will give rise to an anti-parallel orientation of an LNA oligomer when hybridised (with increasing affinity) to either DNA, RNA or another LNA oligomer. It is thus contemplated that an oligomer with xylo configuration ($R^3$=p*) will give rise to a parallel orientation when hybridised to DNA, RNA or another LNA.

In view of the above, it is contemplated that the combination of "normal" LNAs and xylo-LNAs in one oligomer can give rise to interesting properties as long as these monomers of different type are located in domains, i.e. so that an uninterrupted domain of at least 5, such as at least 10, monomers (e.g. xylo-LNA, xylo-nucleotides, etc. monomers) is followed by an uninterrupted domain of at least 5, e.g. at least 10, monomers of the other type (e.g. "normal" LNA, "normal" nucleotides, etc.), etc. Such chimeric type oligomers may, e.g., be used to capture nucleic acids.

In the present context, the term "monomer" relates to naturally occurring nucleosides, non-naturally occurring nucleosides, PNAs, etc. as well as LNAs. Thus, the term "succeeding monomer" relates to the neighbouring monomer in the 5'-terminal direction and the "preceding monomer" relates to the neighbouring monomer in the 3'-terminal direction. Such succeeding and preceding monomers, seen from the position of an LNA monomer, may be naturally occurring nucleosides or non-naturally occurring nucleosides, or even further LNA monomers.

Consequently, in the present context (as can be derived from the definitions above), the term "oligomer" means an oligonucleotide modified by the incorporation of one or more LNA(s).

In the present context, the orientation of the biradical ($R^{2*}$–$R^{4*}$) is so that the left-hand side represents the substituent with the lowest number and the right-hand side represents the substituent with the highest number, thus, when $R^{2*}$ and $R^{4*}$ together designate a biradical "—Q—$CH_2$—", it is understood that the oxygen atom represents $R^{2*}$, thus the oxygen atom is e.g. attached to the position of $R^{2*}$, and the methylene group represents $R^{4*}$.

Considering the numerous interesting possibilities for the structure of the biradical ($R^{2*}$–$R^{4*}$) in LNA(s) incorporated in oligomers, it is believed that the biradical preferably is selected from —(CR*R*)$_r$—Y—(CR*R*)$_s$—, —(CR*R*)$_r$—Y—(CR*R*)$_s$—Y—, —Y—(CR*R*)$_{r+s}$—Y—, —Y—(CR*R*)$_r$—Y—(CR*R*)$_s$—, —(CR*R*)$_{r+s}$—, —Y—, —Y—Y—, wherein each Y is independently selected from —O—, —S—, —Si(R*)$_2$—, —N(R*)—, >C=O, —C(=O)—N(R*)—, and —N(R*)—C(=O)—, each R is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond; and each of r and s is 0–4 with the proviso that the sum r+s is 1–4. Particularly interesting situations are those wherein the biradical is selected from —Y—, —(CR*R*)$_{r+s}$—, —(CR*R*)$_r$—Y—(CR*R*)$_s$—, and —Y—(CR*R*)$_{r+s}$—Y—, wherein and each of r and s is 0–3 with the proviso that the sum r+s is 1–4.

Particularly interesting oligomers are those wherein $R^{2*}$ and $R^{4*}$ in at least one LNA in the oligonmer together designate a biradical selected from —O—, —S—, —N(R*)—, —(CR*R*)$_{r+s+1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR*R*)$_{r+s}$—N(R*)—, —N(R*)—(CR*R*)$_{r+s}$—S—, and —S—(CR*R*)$_{r+s}$—N(R*)—.

It is furthermore preferred that one R is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

In one preferred variant, one group R* in the biradical of at least one LNA is selected from DNA intercalators, photochemically active groups, thermochemically active groups, chelating groups, reporter groups, and ligands (where the latter groups may include a spacer as defined for the substituent B).

Preferably, each of the substituents $R^{1*}$, $R^2$, $R^3$, $R^{3*}$, $R^5$, $R^{5*}$, $R^6$ and $R^{6*}$ of the LNA(s), which are present and not involved in P or P*, is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-aminocarbonyl, $C_{1-6}$-alkylcarbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo, and where $R^{N*}$, when present and not involved in a biradical, is selected from hydrogen and $C_{1-4}$-alkyl.

In a preferred variant of the LNAs, X is selected from —O—, —S—, and —$NR^{N*}$, in particular —O—, and each of the substituents $R^{1*}$, $R^2$, $R^3$, $R^{3*}$, $R^5$, $R^{5*}$, $R^6$ and $R^{6*}$ of the LNA(s), which are present and not involved in P or P*, designate hydrogen.

In an even more preferred variant, X is O, $R^2$ selected from hydrogen, hydroxy, and optionally substituted $C_{1-6}$-alkoxy, one of $R^3$ and $R^{3*}$ is P* and the other is hydrogen, and $R^{1*}$, $R^5$, and $R^{5*}$ designate hydrogen, and, more specifically, the biradical ($R^{2*}$–$R^{4*}$) is selected from —O—, —(CH$_2$)$_{0-1}$—O—(CH$_2$)$_{1-3}$—, —(CH$_2$)$_{0-1}$—S—(CH$_2$)$_{1-3}$—, —(CH$_2$)$_{0-1}$—N($R^N$)—(CH$_2$)$_{1-3}$—, abd —(CH$_2$)$_{2-4}$—, in particular from —O—CH$_2$—, —S—CH$_2$—, and —NR$^H$—CH$_2$—. Generally, with due regard to the results obtained so far, it is preferred that the biradical constituting $R^{2*}$ and $R^{4*}$ forms a two carbon atom bridge, i.e. the biradical forms a five membered ring with the furanose ring (X=O). Particularly interesting are also those oligomers where $R^{2*}$ and $R^{4*}$ of an incorporated LNA of formula I together designate a biradical selected from —O—CH$_2$—, —S—CH$_2$—, and —NR$^H$—CH$_2$—; X is O, B designates a nucleobase selected from adenine, guanine, thymine, cytosine and urasil; $R^2$ is hydrogen, one of $R^3$ or $R^{3*}$ designates P* and the other is hydrogen, and $R^{1*}$, $R^3$, $R^5$, and $R^{5*}$ designate hydrogen.

In these embodiments, it is furthermore preferred that at least one LNA incorporated in an oligomer includes a nucleobase (substituent B) selected from adenine and guanine. In particular, it is preferred that an oligomer have LNA incorporated therein both include at least one nucleobase selected from thymine, urasil and cytosine and at least one nucleobase selected from adenine and guanine. For LNA monomers, it is especially preferred that the nucleobase is selected from adenine and guanine.

Within a variant of these interesting embodiments, all monomers of a oligonucleotide are LNA monomers.

As it will be evident from the general formula I (LNA(s) in an oligomer) and the definitions associated therewith, there may be one or several asymmetric carbon atoms present in the oligomers depending on the nature of the substituents and possible biradicals, cf. below.

In one variant, $R^{3*}$ designates P*. In another variant, $R^3$ designates P*, and in a third variant, some $R^{3*}$ designates P* in some LNAs and $R^3$ designates P* in other LNAs within an oligomer.

The oligomers typically comprise 1–10000 LNA(s) of the general formula I and 0–10000 nucleosides selected from naturally occurring nucleosides and nucleoside analogues. The sum of the number of nucleosides and the number of LNA(s) is at least 2, preferably at least 3, in particular at least 5, especially at least 7, such as in the range of 2–15000, preferably in the range of 2–100, such as 3–100, in particular in the range of 2–50, such as 3–50 or 5–50 or 7–50.

In the present context, the term "nucleoside" means a glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribo-nuclesides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

When considering the definitions and the known nucleosides (naturally occurring and non-naturally occurring) and nucleoside analogues (including known bi- and tricyclic analogues), it is clear that an oligomer may comprise one or more LNA(s) (which may be identical or different both with respect to the selection of substituent and with respect to selection of biradical) and one or more nucleosides and/or nucleoside analogues. In the present context "oligonucleotide" means a successive chain of nucleosides connected via internucleoside linkages, however, it should be understood that a nucleobase in one or more nucleotide units (monomers) in an oligomer (oligonucleotide) may have been modified with a substituent B as defined above.

As mentioned above, the LNA(s) of an oligomer are connected with other monomers via an internucleoside linkage. In the present context, the term "internucleoside linkage" means a linkage consisting of 2 to 4, preferably 3, groups/atoms selected from —CH$_2$—, —O—, —S—, —NR$^H$—, >C=O, >C=NR$^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected form hydrogen and $C_{1-4}$-alkyl, and R" is selected from $C_{1-6}$-alkyl and phenyl. Illustrative examples of such internucleoside linkages are —CH$_2$—CH$_2$—CH$_2$—, —CH$_2$—CO—CH$_2$—, —CH$_2$—CHOH—CH$_2$—, —O—CH$_2$—O—, —O—CH$_2$—CH$_2$—, —O—CH$_2$—CH= (including $R^5$ when used as a linkage to a succeeding monomer), —CH$_2$—CH$_2$—O—, —NR$^H$—CH$_2$—CH$_2$—, —CH$_2$—CH$_2$—NR$^H$—, —CH$_2$—NR$^H$—CH$_2$—, —O—CH$_2$—CH$_2$—NR$^H$—, —NR$^H$—CO—O—, —NR$^H$—CO—NR$^H$—, —NR$^H$—CS—NR$^H$—, —NR$^H$—C(=NR$^H$)—NR$^H$—, —NR$^H$—CO—CH$_2$—NR$^H$—, —O—CO—O—, —O—CO—CH$_2$—O—, —O—CH$_2$—CO—O—, —CH$_2$—CO—NR$^H$—, —O—CO—NR$^H$—, —NR$^H$—CO—CH$_2$—, —O—CH$_2$—CO—NR$^H$—, —O—CH$_2$—CH$_2$—NR$^H$—, —CH=N—O—, —CH$_2$—NR$^H$—O—, —CH$_2$—O—N= (including $R^5$ when used as a linkage to a succeeding monomer), —CH$_2$—O—NR$^H$—, —CO—NR$^H$—CH$_2$—, —CH$_2$—NR$^H$—O—, —CH$_2$—NR$^H$—CO—, —O—NR$^H$—CH$_2$—, —O—NR$^H$—, —O—CH$_2$—S—, —S—CH$_2$—O—, —CH$_2$—CH$_2$—S—, —O—CH$_2$—CH$_2$—S—, —S—CH$_2$—CH= (including $R^5$ when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NR$^H$—, —NR$^H$—S(O)$_2$—CH$_2$—, —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R')—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—NR$^H$—, —NR$^H$—P(O)$_2$—O—, —O—P(O,NR$^H$)—O—, —CH$_2$—P(O)$_2$—O—, —O—P(O)$_2$—CH$_2$—, and —O—Si(R")$_2$—O—; among which —CH$_2$—CO—NR$^H$—, —CH$_2$—NR$^H$—O—, —S—CH$_2$—O—, —O—P(O)$_2$—O—, —O—P(O,S)—O—, —O—P(S)$_2$—O—, —NR$^H$—P(O)$_2$—O—, —O—P(O,NR$^H$)—O—, —O—PO(R")—O—, —O—PO(CH$_3$)—O—, and —O—PO(NHR$^N$)—O—, where $R^H$ is selected form hydrogen and $C_{1-4}$alkyl, and R" is selected from $C_{1-6}$alkyl and phenyl, are especially preferred. Further illustrative examples are given in Mesmaeker et. al., Current Opinion in Structural Biology 1995, 5, 343–355. The left-hand side of the internucleoside linkage is bound to the 5-membered ring as substituent P*, whereas the right-hand side is bound to the 5'-position of a preceding monomer.

It is also clear from the above that the group P may also designate a 5'-terminal group in the case where the LNA in question is the 5'—terminal monomer. Examples of such 5'-terminal groups are hydrogen, hydroxy, optionally substituted $C_{1-6}$-alkyl, optionally substituted $C_{1-6}$-alkoxy, optionally substituted $C_{1-6}$—alkylcarbonyloxy, optionally substituted aryloxy, monophosphate, diphosphate, triphosphate, and —W—A', wherein W is selected from —O—, —S—, and —N($R^H$)— where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In the present description and claims, the terms "monophosphate", "diphosphate", and "triphosphate" mean groups of the formula: —O—P(O)$_2$—O$^-$—, —O—P(O)$_2$—O—P(O)$_2$—O$^-$—, and —O—P(O)$_2$—O—P(O)$_2$—O—P(O)$_2$—O$^-$—, respectively.

In a particularly interesting embodiment, the group P designates a 5'-terminal groups selected from monophosphate, diphosphate and triphosphate. Especially the triphosphate variant is interesting as a substrate for nucleic acid polymerases.

Analogously, the group P* may designate a 3'-terminal group in the case where the LNA in question is the 3'-terminal monomer. Examples of such 3'-terminal groups are hydrogen, hydroxy, optionally substituted $C_{1-6}$-alkoxy, optionally substituted $C_{1-6}$-alkylcarbonyloxy, optionally substituted aryloxy, and —W—A', wherein W is selected from —O—, —S—, and —N($R^H$)— where $R^H$ is selected from hydrogen and $C_{1-6}$-alkyl, and where A' is selected from DNA intercalators, photochemically active groups, thermochemically active groups, chelating groups, reporter groups, and ligands (where the latter groups may include a spacer as defined for the substituent B).

In a preferred variant of the LNAs, the oligomer has the following formula V:

G-[Nu-L]$_{n(O)}$-{[LNA-L]$_{m(q)}$-[Nu-L]$_{n(q)}$}$_q$-G*    V wherein q is 1–50;

each of n(0), . . . , n(q) is independently 0–10000;

each of m(1), . . . , m(q) is independently 1–10000;

with the proviso that the sum of n(0), . . . , n(q) and m(1), . . . , m(q) is 2–15000;

G designates a 5'-terminal group;

each Nu independently designates a nucleoside selected from naturally occurring nucleosides and nucleoside analogues;

each LNA independently designates a nucleoside analogue;

each L independently designates an internucleoside linkage between two groups selected from Nu and LNA, or L together with G* designates a 3'-terminal group; and each LNA-L independently designates a nucleoside analogue of the general formula I as defined above.

Within this variant, as well as generally, the LNAs preferably include different nucleobases, in particular both nucleobases selected from thymine, cytosine and urasil and nucleobases selected from adenine and guanine.

The oligomers are also intended to cover chimeric oligomers. "Chimeric oligomers" means two or more oligomers with monomers of different origin joined either directly or via a spacer. Illustrative examples of such oligomers which can be combined are peptides, PNA-oligomers, oligomers containing LNA's, and oligonucleotide oligomers. The combination of an oligomer having xylo-LNA (R$^3$=P*) domain(s) and "normal" LNA (R$^3$=P*) domain(s) might be construed as an example of a chimeric oligomer as the various domains may have different affinity and specificity profiles.

Generally, the oligomers have surprisingly good hybridisation properties with respect to affinity and specificity. Thus, the oligomers comprise at least one nucleoside analogue which imparts to the oligomer a $T_m$ with a complementary DNA oligonucleotide which is at least 2.5° C. higher, preferably at least 3.5° C. higher, in particular at least 4.0° C. higher, especially at least 5.0° C. higher, than that of the corresponding unmodified reference oligonucleotide which does not comprise any nucleoside analogue. In particular, the $T_m$ of the oligomer is at least 2.5×N° C. higher, preferably at least 3.5×N° C. higher, in particular at least 4.0×N° C. higher, especially at least 5.0×N° C. higher, where N is the number of nucleoside analogues.

In the case of hybridisation with a complementary RNA oligonucleotide, the at least one nucleoside analogue imparts to the oligomer a $T_m$ with the complementary DNA oligonucleotide which is at least 4.0° C. higher, preferably at least 5.0° C. higher, in particular at least 6.0° C. higher, especially at least 7.0° C. higher, than that of the corresponding unmodified reference oligonucleotide which does not comprise any nucleoside analogue. In particular, the $T_m$ of the oligomer is at least 4.0×N° C. higher, preferably at least 5.0×N° C. higher, in particular at least 6.0×N° C. higher, especially at least 7.0×N° C. higher, where N is the number of nucleoside analogues.

The term "corresponding unmodified reference oligonucleotide" is intended to mean an oligonucleotide solely consisting of naturally occurring nucleotides which represents the same nucleobases in the same absolute order (and the same orientation).

The $T_m$ is measured under one of the following conditions:

a) 10 mM Na$_2$HPPO$_4$, pH 7.0, 100 mM NaCl, 0.1 mM EDTA;

b) 10 mM Na$_2$HPO$_4$ pH 7.0, 0.1 mM EDTA; or c) 3M tetrametylammoniumchlorid (TMAC), 10 mM Na$_2$HPO$_4$, pH 7.0, 0.1 mM EDTA;

preferably under conditions a), at equimolar amounts (typically 1.0 µM) of the oligomer and the complementary DNA oligonucleotide.

The oligomer is preferably as defined above, where the at least one nucleoside analogue has the formula I where B is a nucleobase. In a particularly interesting embodiment at least one nucleoside analogue includes a nucleobase selected from adenine and guanine.

Furthermore, with respect to specificity and affinity, the oligomer, when hybridised with a partially complementary DNA oligonucleotide, or a partially complementary RNA oligonucleotide, having one or more mismatches with said oligomer, should exhibit a reduction in $T_m$, as a result of said mismatches, which is equal to or greater than the reduction which would be observed with the corresponding unmodified reference oligonucleotide which does not comprise any nucleoside analogues. Also, the oligomer should have substantially the same sensitivity of $T_m$ to the ionic strength of the hybridisation buffer as that of the corresponding unmodified reference oligonucleotide.

Oligomers defined herein are typically at least 1% modified, such as at least 2% modified, e.g. 3% modified, 4% modified, 5% modified, 6% modified, 7% modified, 8% modified, or 9% modified, at least 10% modified, such as at least 11% modified, e.g. 12% modified, 13% modified, 14% modified, or 15% modified, at least 20% modified, such as at least 30% modified, at least 50% modified, e.g. 70% modified, and in some interesting applications 100% modified.

The oligomers preferably has substantially higher 3'-exonucleolytic stability than the corresponding unmodified reference oligonucleotide.

It should be understood that oligomers (wherein LNAs are incorporated) and LNAs as such include possible salts thereof, of which pharmaceutically acceptable salts can be relevant. Salts include acid addition salts and basic salts. Examples of acid addition salts are hydrochloride salts, sodium salts, calcium salts, potassium salts, etc. Examples of basic salts are salts where the (remaining) counter ion is selected from alkali metals, such as sodium and potassium, alkaline earth metals, such as calcium, and ammonium ions ($^+N(R^g)_3R^h$, where each of $R^g$ and $R^h$ independently designates optionally substituted $C_{1-6}$-alkyl, optionally substituted $C_{2-6}$-alkenyl, optionally substituted aryl, or optionally substituted heteroaryl). Pharmaceutically acceptable salts are, e.g., those described in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology. Thus, the term "an acid addition salt or a basic salt thereof" used herein is intended to comprise such salts. Furthermore, the oligomers and LNAs as well as any intermediates or starting materials therefor may also be present in hydrate form.

FIGURE LEGENDS

FIG. 1 Illustrate that only LNA primers with a matching 3'-end serve as primers in PCR.

Figure 2:
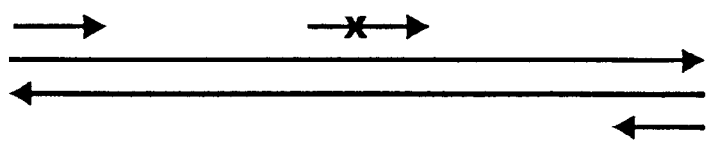
Figure 2:
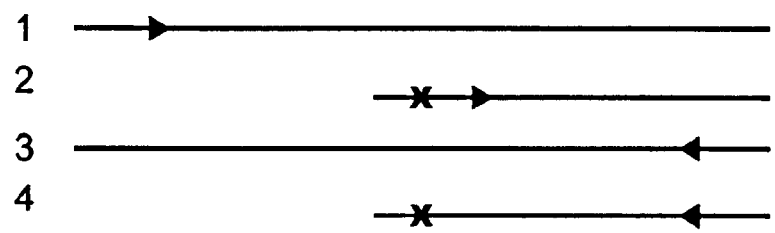
Figure 2:
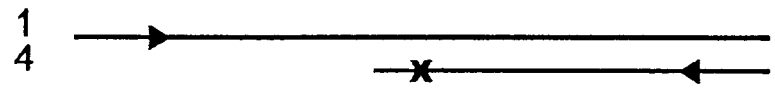

FIG. 2 Oligonucleotide-directed single base mutation obtained by incorporating 3 DNA oligos in the PCR reaction.

A) Starting with 3 oligonucleotides two stranded PGR primers and one mutation oligo, the mismatching base id indicated with X.

B) After 2 cycles of PCR 4 single-stranded PCR products are generated.

C) Product 1 and 4 generate a double-stranded PCR product containing the expected mutation after few additional PCR cycles.

Figure 3:
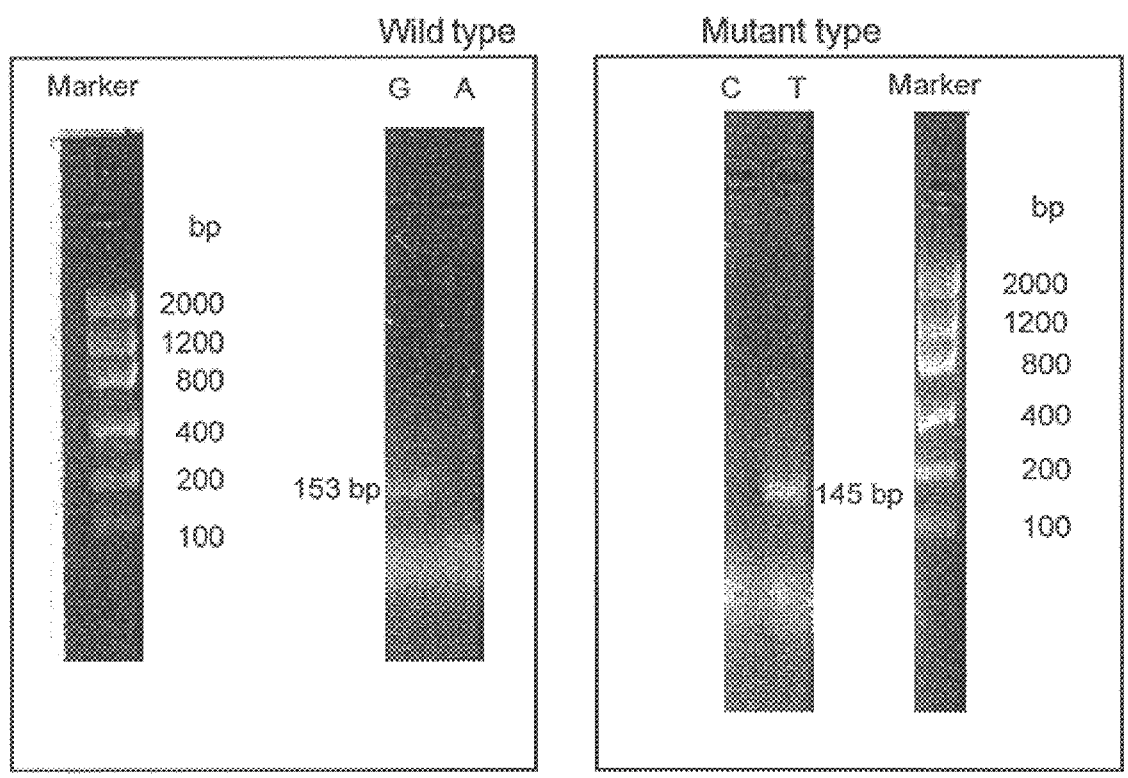

FIG. 3 Allele specific PCR with LNA primers. Left panel shows the results with primer-set EQ3053/EQ3213, the "Wild type" reaction. "G" signify that the "G-allele" of the ApoB gene was used as template, "A" that the "A-allele" of the ApoB gene was used. Right panel shows the results with primer-set EQ3157/EQ3176, the "Mutant type" reaction. Note that the primers are directed towards the non-coding strand. "C" signifies that the wildtype "G-allele" of the ApoB gene was used as template, "T" that the mutant "A-allele" of the ApoB gene was used. Marker is the Low DNA Mass™ (GibcoBRL cat. no. 10068-013, Life Technologies Inc., Rockville, Md., USA).

Figure 4:
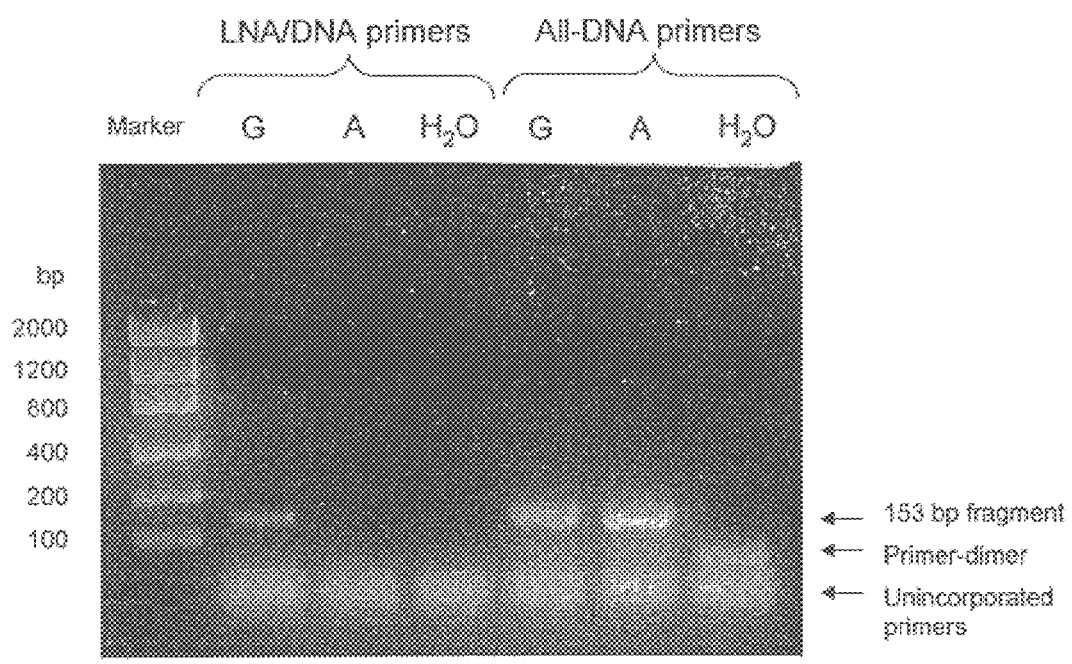

FIG. 4 Comparison of LNA and DNA primers. Left panel shows the results with the LNA/DNA primer-set EQ3053/EQ3213. Right panel shows the results with all-DNA primer-set EQ3647/EQ3213. "G" signify that the "G-allele" of the ApoB gene was used as template, "A" that the "A-allele" of the ApoB gene and "H$_2$O" that no template was included in the PCR reaction. Marker is the Low DNA Mass™ (GibcoBRL cat. no. 10068-013, Life Technologies Inc., Rockville, Md., USA).

Figure 5:
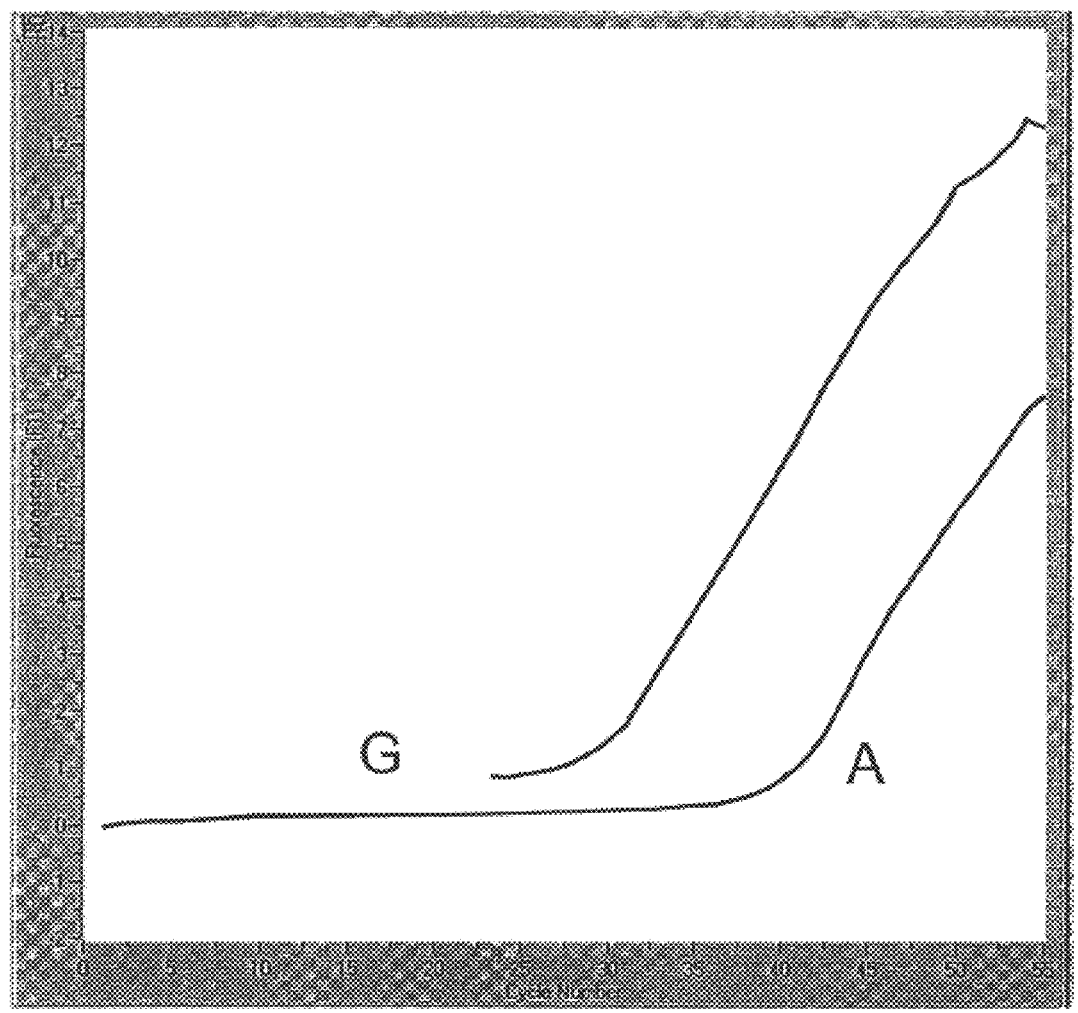

FIG. 5. Cycle-by-cycle monitoring of the amplification process. The increase in fluorescence during amplification of the "G-allele" (G, upper curve) and "A-allele" (A, lower curve) using the EQ3053/EQ3213 primer set and either the "A-allele" plasmid or the "G-allele" plasmid as template.

Figure 6:
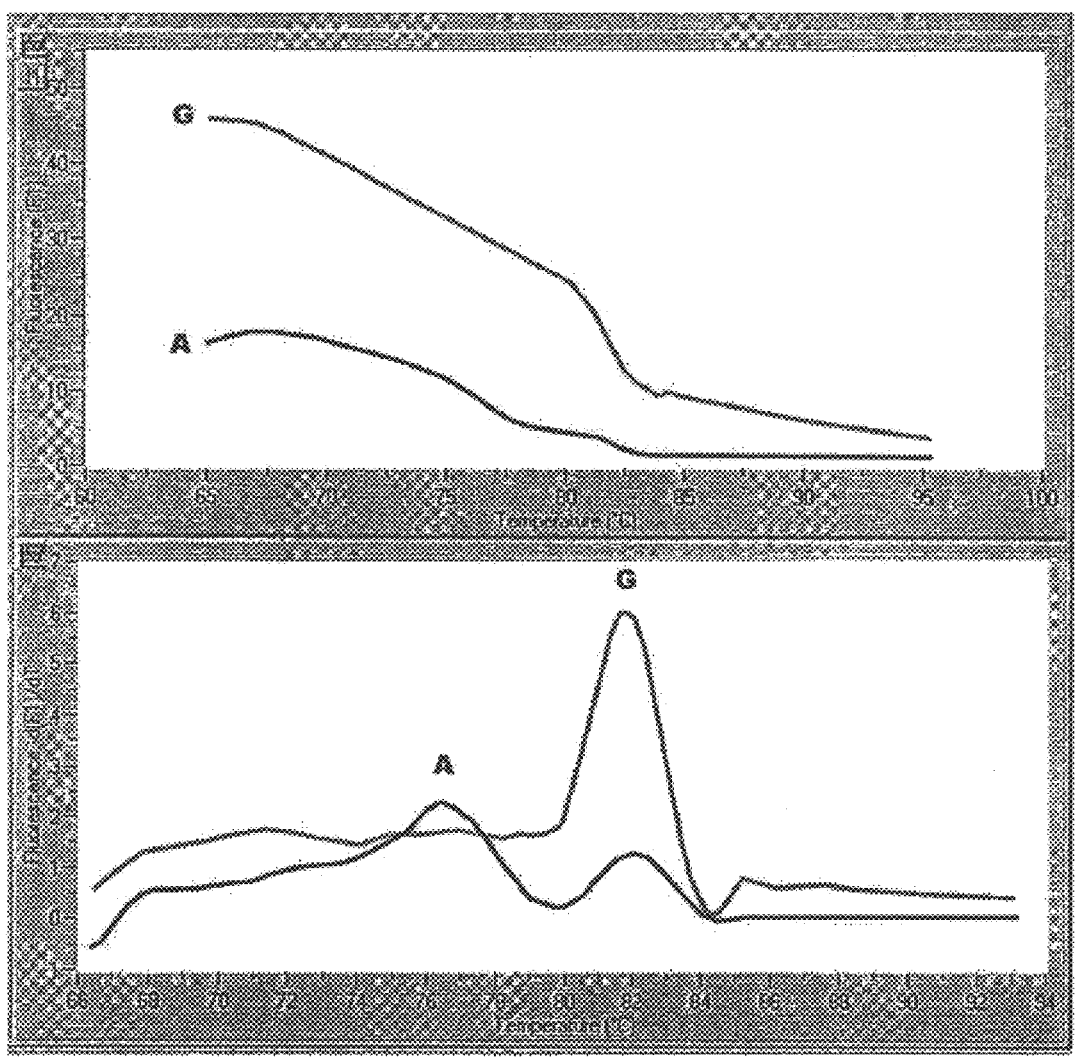

FIG. 6. Melting curve analysis of PCR fragments generated with the EQ3053/EQ3213 primer set and either the "A-allele" template (A, lower curve) or the "G-allele" template (G, upper curve). The upper panel shows the fluorescence of the SyBR Green I dye bound to double-stranded amplicon. The lower panel shows the first negative derivative (−dF/dT) of the melting curve in upper panel. The $T_m$ is seen as the peak on the −dF/dT plotting.

EXAMPLES

Example 1

Sequence Specific Amplification with LNA Primers
Synthesis and Analysis of Primers Standard coupling conditions according to the protocol (0.2 μmol scale) of the DNA-synthesizer (Pharmacia Gene Assembler Special®, Pharmacia AB, Uppsala, Sweden) were used except that the coupling time for LNA amidites was increased from the standard two minutes to five minutes. The step-wise coupling yield was approximately 99%. Standard 2'-deoxynucleoside CPG or polystyrene solid supports were generally used. After completion of the desired sequences, cleavage from the solid support and removal of protecting groups was accomplished using 32% aqueous ammonia (55° C. for 5 or 10 h). LNAs synthesized in the 5'-0-DMT-ON mode were purified by reversed-phase HPLC (Delta Pak C-18, 300A, column dimensions 0.4×30 cm) in a concentration gradient of acetonitrile in 0.05 M triethylammonium acetate buffer pH 7.0 (flow rate 1.5 cm /min). Fractions containing 5'-0-DMT-ON LNAs (retention times of 30–35 minutes) were evaporated and detritylated in 80% acetic acid (1 cm, room temperature, 1 h). After evaporation, the LNAs were re-purified by reversed-phase HPLC (eluting as single peaks) as described above.

Sample Preparation

Human genomic DNA was isolated from 5 mL full blood, using the DNA Isolation Kit for Mammalian Blood (Roche Molecular Systems cat. no. 1 667 327. Roche Molecular Biochemicals, Hvidovre, Denmark) and closely following the recommendations of the manufacturer.

The "G-allele" of the ApoB gene was generated by PCR-amplification of part of the wild type human ApoB gene comprising the ApoB3500 locus (Ludwig et al. (1987) DNA 6: 363–372; accession no. M19828, SEQ ID ON 4). The PCR fragment was cloned into plasmid pCR®2.1-TOPO using the TOPO® TA Cloning® Kit (Invitrogen, cat. no. K4500-01, Invitrogen Corporation, Carlsbad Calif. USA). Plasmid DNA were purified from bacterial cultures, using QUIAGEN® Plasmid Kits (QIAGEN GmbH, Hilden, Germany). The DNA sequence of the insert was verified by DNA sequencing using a ALFexpress II DNA Analysis System (Amersham Pharmacia Biotech) and closely following the recommendations of the manufacturer.

PCR Amplification

The PCR reaction was carried out in 0.5 mL thin-wall tubes using a Hybaid PCR Express thermocycler (Hybaid, Middlesex, UK). The dNTPs were from Amersham Pharmacia Biotech AB, Uppsala, Sweden. The final reagent mixture was composed as follows:

dATP, dGTP, dTTP, dCTP: 200 μM of each 1.5 mM MgCl2

5 μL 10×GeneAmp PCR Buffer (Perkin-Elmer Corporation, Norwalk, Conn.,USA).

1 μM primer EQ 3053, SEQ ID NO 1

1 μM primer EQ 3054, SEQ ID NO 2

1 unit AmpliTaq Gold® polymerase (Perkin Elmer cat. no. N808-0240, Perkin-Elmer Corporation, Norwalk, Conn., USA).

2 μL DNA template in serial dilutions, see FIG. 1.

50 μL Total Volume Thermocycling

Denaturating: 95° C. 15 min

Cycling: 35 times (30 sec. at 94° C.; 30 sec. at 63° C.; 30 sec. at 72° C.)

Final extension: 10 min. 72° C.

Cool down to 4° C.

Detection of Extension Products

10 μL of the PCR products were subsequently mixed with 2 μL application buffer (40% sucrose, 0.25% bromophenol blue, 0.25% xylene cyanol, 0.1 M EDTA pH 8.0) and electrophoresed in agarose gel. The gel was composed of 1% SeaKem®, Agarose (FMC Bio-Products, Philadelphia, Pa., USA) in 1×TAE, 0.5 μg/mL ethidium bromide (Sigma-Aldrich cat. no. E7637, Sigma-Aldrich Denmark A/S, Vallensbaek Strand, Denmark) (50×TAE=242 g Tris Base, 57.1 mL glacial acetic acid, 100 mL 0.5 M EDTA pH 8.0). The gels run for 0.5–1 h at approximately 5 V/cm. Fluorescence was photographed at using a Image-Master VDS equipment (Amersham Pharmacia Biotech AB, Uppsala, Sweden). A typical experiment is shown in FIG. 1.

To establish if 3'-terminal substitutions in PCR-primers with LNA-monomers can furnish allele specific amplification the template DNA's were amplified with the aid of the two sets of primers EQ3053/ApoBR2 and EQ3054/ApoBR2. The primer-set EQ3053/ApoBR2 (SEQ ID NO 1, SEQ ID NO 3) produce a 667 bp PCR product provided the "G-allele" of the ApoB gene (SEQ ID NO 4) is used as template, whereas the EQ3053/ApoBR2 primerset does not produce any specific PCR product when 30.4 ng or less of the ApoB gene "A-alleles" (SEQ ID NO 5) is used as template. The results are shown in FIG. 1.

EQ3053 (SEQ ID NO 1): 5'-CCT ACT TGA ATT CCA AGA GCA CAC G$^{LNA}$-3'

EQ3054 (SEQ ID NO 2): 5'-CCT ACT TGA ATT CCA AGA GCA CAC A$^{LNA}$-3'

ApoBR2 (SEQ ID NO 3): 5'-TTT AGA TCA TTT AGT TTC AGC CC-3'

"G-allele" of the ApoB gene (SEQ ID NO 4):

5'-CTTACTTGAA TTCCAAGAGC ACAC<u>G</u>GTCTT CAGTGAAGCT GCAGGGCACT-3'

"A-allele" of the ApoB gene (SEQ ID NO 5):

5'-CTTACTTGAA TTCCAAGAGC ACAC<u>A</u>GTCTT CAGTGAAGCT GCAGGGCACT-3'

Example 2

Detection of the ApoB R3500Q Mutation by Allele Specific PCR with LNA-primers

Apolipoprotein B (ApoB) is the non-exchangeable protein of the low density lipoprotein (LDL) complex that is recognised by the LDL-receptor. Familial defective ApoB 100 is an autosomal dominant disorder caused by a base transition (G→A mutation) at amino acid 3500 (arg→gin)— the ApoB R3500Q mutation. The mutation reduces the affinity of LDL complex for the LDL-receptor and results in elevated levels of LDL cholesterol in plasma. The prevalence rate of the mutation is 1:500 for heterozygotes and 1:1,000,000 for homozygotes in the normal population (Harrison's Principles of Internal Medicine, 14th edition. by Fauci, A. S. et al. (Eds.) McGraw Hill).

To demonstrate the versatility of PCR with LNA-primers two allele specific PCRs have been set up which allow positive identification of both the "G-allele" and the "A-allele" of the ApoB R3500Q polymorphism.

Synthesis and Analysis of Primers

Synthesis and analysis of LNA primers was carried out essentially as described in example 1. Downstream DNA primers were obtained as HPLC purified oligos from a commercial source (DNA Technology, Aarhus, Denmark).

Sample Preparation

The "G-allele" of the ApoB gene was generated by PCR-amplification of part of the wild type human ApoB gene comprising the ApoB3500 locus as described in example 1. Using the "G-allele" plasmid, the "A-allele" of the ApoB gene was generated by creating a oligonucleotide-directed single base mutation (G→A mutation) at amino acid 3500 during PCR-amplification of part of the wild type human ApoB gene comprising the ApoB3500 locus (SEQ ID NO 4). The oligonucleotide-directed single base mutation was obtained by incorporating 3 DNA oligos in the PCR reaction, two amplification oligos and one oligo covering the site to be mutated, this oligo contained one mismatch where the mutation was generated. The principle is illustrated in FIG. 2. Following the PCR amplification fragments were cloned into plasmid pCR®2.1-TOPO using the TOPO™ TA Cloning® Kit (Invitrogen, cat. no. K4500-01, Invitrogen Corporation, Carlsbad Calif. USA). Plasmid DNA were purified from cloned bacterial cultures, using QUIAGEN® Plasmid Kits (QIAGEN GmbH, Hilden, Germany). Plasmid preparations were then screened for presence of the expected mutation by DNA sequencing using a ALFexpress II DNA Analysis System (Amersham Pharmacia Biotech AB, Uppsala, Sweden) and closely following the recommendations of the manufacturer.

PCR Amplification

The PCR reactions were carried out in 0.5 mL thin-wall tubes using an Eppendorf Mastercycler Gradient thermocycler (Eppendorf—Netheler—Hinz GmbH, Hamburg, Germany). The dNTP's were from Amersham Pharmacia Biotech AB, Uppsala, Sweden. The final reagent mixture was composed as follows:

PROCEDURE for the Detection of the Wildtype (G-allele) of the Human ApoB3500 Locus.

dATP, dGTP, dTTP, dCTP: 200 μM of each 1.5 mM MgCl2

5 μL 10×GeneAmp PCR Buffer (Perkin-Elmer Corporation, Norwalk, Conn., USA).

1 μM primer EQ 3053, SEQ ID NO 1

1 μM primer EQ 3213, SEQ ID NO 6

1 unit AmpliTaq Gold® polymerase (Perkin Elmer cat. no. N808-0240, Perkin-Elmer Corporation, Norwalk, Conn., USA).

2 μL DNA template (approximately 50 ng plasmid/μL).

50 μL total volume

Both the "G-allele" and the "A-allele" of the human ApoB gene generated by PCR-amplification and cloned into plasmid pCR®2.1-TOPO was used.

Thermocycling

Denaturating: 95° C. 15 min

Cycling: 35 times (30 sec. at 94° C.; 30 sec. at 55° C.; 30 sec. at 72° C.)

Final extension: 10 min. 72° C.

Cool down to 4° C.

Detection

The PCR products were subsequently analysed by standard agarose gel electrophoresis (see example 1). Only difference was 2% agarose, and stained by including Gel-Staro® (FMC BioProducts, Rockland, Me., USA) diluted 1:30.000 in the gel. For permanent record the gel was photographed by standard Polaroid (Polaroid LTD., St. Albans, UK) photography using an appropriate UV-transilluminator (Model TM-20E UV Products, Upland, Calif., USA) and filter (Kodak Wratten #9 Eastman Kodak Co., Rochester, N.Y., USA).
PROCEDURE for the Detection of the Mutant Type (A-allele) of the Human ApoB3500 Locus
dATP, dGTP, dTTP, dCTP: 200 µM of each
1.5 mM MgCl2
5 µL 10×GeneAmp PCR Buffer (Perkin-Elmer Corporation, Norwalk, Conn.,USA).
1 µM primer EQ 3157, SEQ ID NO 7
1 µM primer EQ 3176, SEQ ID NO 8
1 unit AmpliTaq Gold® polymerase (Perkin Elmer cat. no. N808-0240, Perkin-Elmer Corporation, Norwalk, Conn., USA).
2 µL DNA template (approximately 50 ng plasmid/µL).
50 µL total volume
Both the "G-allele" and the "A-allele" of the human ApoB gene generated by PCR-amplification and cloned into plasmid pCR®2.1-TOPO was used
Thermocycling
Denaturating: 95° C. 15 min
Cycling: 35 times (30 sec. at 94° C.; 30 sec. at 67° C.; 30 sec. at 72° C.)
Final extension: 10 min. 72° C.
Cool down to 4° C.
Detection The PCR products were subsequently analysed by standard agarose gel electrophoresis (see example 1). Only difference was 2% agarose, and stained by including GelStar® (FMC BioProducts, Rockland, Me., USA) diluted 1:30.000 in the gel. For permanent record the gel was photographed by standard Polaroid (Polaroid LTD., St. Albans, UK) photography using an appropriate UV-transilluminator (Model TM-20E UV Products, Upland, Calif., USA) and filter (Kodak Wratten #9 Eastman Kodak Co., Rochester, N.Y., USA).
Results To show that 3'-terminal substitutions in PCR-primers with LNA-monomers can furnish allele specific amplification template DNA's containing both the "G-allele" and the "A-allele" of the human ApoB gene were amplified with the aid of the two sets of primers EQ3053/EQ3213 and EQ 3157/EQ 3176.
EQ3053 (SEQ ID NO 1): 5'-CCT ACT TGA ATT CCA AGA GCA CAC $G^{LNA}$-3'
EQ3213 (SEQ ID NO 6): 5'-GTT TTT CGT ACT GTG CTC CCA GAG-3'
EQ3157 (SEQ ID NO 7): 5'-CCC TGC AGC TTC ACT GAA GAC $T^{LNA}$-3'
EQ3176 (SEQ ID NO 8): 5'-CAC CTC TTA CTT TTC CAT TGA GT-3'
"G-allele" of the ApoB gene (SEQ ID NO 4):
  5'-CTTACTTGAA TTCCAAGAGC ACAC<u>G</u>GTCTT CAGTGAAGCT GCAGGGCACT-3'
"A-allele" of the ApoB gene (SEQ ID NO 5):
  5'-CTTACTTGAA TTCCAAGAGC ACAC<u>A</u>GTCTT CAGTGAAGCT GCAGGGCACT-3'

The primer-set EQ3053/EQ3213 (SEQ ID NO 1, SEQ ID NO 6) produce a 153 bp PCR product provided the "G-allele" of the ApoB gene (SEQ ID NO 4) was used as template, whereas the primer-set does not produce any specific PCR product when the ApoB gene "A-allele (SEQ ID NO 5) was used as template—see FIG. 3.

The primer-set EQ3157/EQ3176 (SEQ ID NO 7, SEQ ID NO 8) produce a 145 bp PCR product provided the "mutant" or "A-allele" of the ApoB gene (SEQ ID NO 5) was used as template, whereas the primer-set does not produce any specific PCR product when the "wild type" or "G-allele" of the ApoB gene (SEQ ID NO 4) was used as template—see FIG. 3. Note that the two primer-sets EQ3053/EQ3213 and EQ3157/EQ3176 are directed towards different strands of the template molecule.

Example 3
DNA Primers can not Discriminate Between Wildtype and Mutant Type

To evalute the difference between LNA and DNA primers the two PCR reactions was set up.

One reaction was the reaction described in example 2 for the detection of the wildtype (G-allele) of the human ApoB3500 locus using LNA-primer EQ 3053.

The other reaction was similar but instead of using LNA-primer EQ 3053 a DNA primer with a sequence similar to EQ 3053 was used.
Synthesis and Analysis of Primers Synthesis and analysis of LNA primers was carried out essentially as described in example 1. DNA primers were obtained as HPLC purified oligos from a commercial source (DNA Technology, Aarhus, Denmark).
PCR Amplification The PCR reactions were carried out in 0.5 mL thin-wall tubes using an Eppendorf Mastercycler Gradient thermocycler (Eppendorf—Netheler—Hinz GmbH, Hamburg, Germany). The dNTP's were from Amersham Pharmacia AB, Uppsala, Sweden. The final reagent mixture was composed as follows:

The reaction with LNA-primer contained 1 µM of primer EQ 3053 (SEQ ID NO 1) and 1 µM of primer EQ 3213 (SEQ ID NO 6).

The reaction with DNA-primers contained 1 µM of primer EQ 3647 (SEQ ID NO 9) and 1 µM of primer EQ 3213 (SEQ ID NO 6).

In all other respects the reactions with LNA and DNA were identical, being:
dATP, dGTP, dTTP, dCTP: 200 µM of each
1.5 mM MgCl2
5 µL 10×GeneAmp PCR Buffer (Perkin-Elmer Corporation, Norwalk, Conn.,USA).
1 unit AmpliTaq Gold® polymerase (Perkin Elmer cat. no. N808-0240, Perkin-Elmer Corporation, Norwalk, Conn., USA).
2 µL DNA template (approximately 50 ng plasmid/µL).
50 µL total volume Both the "G-allele" and the "A-allele" templates of the human ApoB gene were the plasmids discussed in Example 2.
Thermocycling
Denaturing: 95° C. 15 min
Cycling: 35 times (30 sec. at 94° C.; 30 sec. at 55° C.; 30 sec. at 72° C.)
Final extension: 10 min. 72° C.
Cool down to 4° C.
Detection The PCR products were subsequently analysed by standard agarose gel electrophoresis in 2% agarose, and stained with GelStar® (FMC BioProducts, Rockland, Me., USA) as described in Example 2. Finally the gel was photographed as described in Example 2.
Results As seen in FIG. 4 the primer-set EQ3053/EQ3213 (SEQ ID NO 1, SEQ ID NO 6) produced a 153 bp PCR product when the "G-allele" of the ApoB gene (SEQ ID NO 4) was used as template, whereas the primer-set did not produce any specific PCR product when the ApoB gene "A-allele (SEQ ID NO 5) was used as template—see FIG. 4.

EQ3053 (SEQ ID NO 1): 5'-CCT ACT TGA ATT CCA AGA GCA CAC G$^{LNA}$-3'

EQ3213 (SEQ ID NO 6): 5'-GTT TTT CGT ACT GTG CTC CCA GAG-3'

"G-allele" of the ApoB gene (SEQ ID NO 4):
5'-CTTACTTGAA TTCCAAGAGC ACAC<u>G</u>GTCTT CAGTGAAGCT GCAGGGCACT-3'

"A-allele" of the ApoB gene (SEQ ID NO 5):
5'-CTTACTTGAA TTCCAAGAGC ACAC<u>A</u>GTCTT CAGTGAAGCT GCAGGGCACT-3'

The all-DNA primer-set EQ3647/EQ3213 (SEQ ID NO 9, SEQ ID NO 6) however produced a 153 bp PCR product when both the "G-allele" or the "A-allele was used as template—see FIG. 4.

EQ3647 (SEQ ID NO 9): 5'-CCT ACT TGA ATT CCA AGA GCA CAC G-3'

EQ3213 (SEQ ID NO 6): 5'-GTT TTT CGT ACT GTG CTC CCA GAG-3'

We conclude that the LNA-primer but not the similar DNA-primer can detect the single base difference of the ApoB R3500Q mutation.

Example 4
Sequence Specific Amplification with LNA Primer Applied on the Roche Lightcycler To illustrate the flexibility of PCR with LNA-primers an allele specific PCR have been set up on the LightCycler (Roche Diagnostics GmbH, Mannheim, Germany). The LightCycler instrument is a device that allows amplification and identification of produced PCR products by $T_m$ measurements in one working operation.

The reaction that allows positive identification of the "G-allele" of the human ApoB R3500Q polymorphism was as follows:

Synthesis and Analysis of Primers

Synthesis and analysis of LNA primers was carried out essentially as described in example 1. DNA primers were obtained as HPLC purified oligos from a commercial source (DNA Technology, Aarhus, Denmark).

PCR Amplification

The PCR reactions were carried out in the borosilicate glass capillaries provided with the instrument and closely following the recommendations of the manufacturer.

Each Reaction Contained
2 μL LightCycler—DNA Master SyBR Green I mix (Roche Diagnostics GmbH, Mannheim, Germany). The master-mix contains nucleotides, PCR buffer, SyBR Green and Taq polymerase.
1 μL DNA template (approximately 50 ng plasmid/μL).
1 μM of primer EQ 3053 (SEQ ID NO 1) and 1 μM of primer EQ 3213 (SEQ ID NO 6).
3 mM $MgCl_2$
In 20 μL total volume.

Either the "G-allele" or the "A-allele" plasmids were added as template. Both the "G-allele" and the "A-allele" templates of the human ApoB gene were the plasmids discussed in Example 2.

Thermocycling
Denaturing: 95° C. 2 min, 20° C./sec
Cycling: 44 times (0 sec. setting at 95° C.; 5 sec. at 55° C.; 7 sec. at 72° C.)

$T_m$ Measurement
Segment 1: 95° C., 0 sec. setting.
Segment 2: 65° C., 10 sec.
Segment 3: 95° C., 0 sec. setting, 0.1° C./sec. continues measurement.
Cooling: 40° C., 30 sec Results The primer-set EQ3053/EQ3213 (SEQ ID NO 1, SEQ ID NO 6) clearly amplified the "G-allele" whereas only very little PCR product was observed when the "A-allele" was used as template—see FIG. 5.

As seen in FIG. 6 the primer-set EQ3053/EQ3213 produced a PCR product with a well defined $T_m$ of 82° C.

We conclude that the EQ3053/EQ3213 primer-set can be used for allele specific amplification in the LightCycler.

What is claimed is:

1. A method for detecting in a sample the presence of a nucleic acid Q' whose nucleotide sequence differs from a nucleic acid Q in at least one position A, the method comprising the steps of
   a) combining nucleic acids present in the sample with an appropriate amount of nucleoside triphosphates, an agent for polymerisation of the nucleoside triphosphates and at least one diagnostic oligonucleotide containing at position A a nucleotide which is capable of hybridizing to the nucleotide at position A of nucleic acid Q' but not to a nucleotide at position A of nucleic acid Q under hybridisation conditions, the at least one diagnostic oligonucleotide containing at least one LNA,
   b) extending any oligonucleotides which hybridize to the nucleic acids present in the sample to form extension products, wherein said nucleic acids are used as templates,
   c) detecting any nucleic acids formed in step b) and thereby the presence of nucleic acid Q' in the sample.

2. A method for detecting in a sample the presence of a nucleic acid Q' whose nucleotide sequence differs from a nucleic acid Q in at least one position A, the method comprising the steps of
   a) combining nucleic acids present in the sample with an appropriate amount of nucleoside triphosphates, an agent for polymerisation of the nucleoside triphosphates and at least one diagnostic oligonucleotide containing at position A a nucleotide which is capable of hybridising to the nucleotide at position A of nucleic acid q under hybiridisation conditions, the at least one diagnostic oligonucleotide containing at least one LNA,
   b) extending an oligonucleotide which hybridises to the nucleic acids present in the sample to form extension products, wherein said nucleic acids are used as templates,
   c) after the formation of extension products treating the reaction mixture under denaturing conditions to separate the extension products from the template,
   d) hybridising in the presence of an appropriate amount of nucleoside triphosphate and an agent for polymerisation of the nucleoside triphosphates the single stranded nucleic acids of step c) with at least one diagnostic oligonucleotide containing at position A a nucleotide which is capable of hybridizing to the nucleotide at position A of nucleic acid Q' but not to a nucleotide at position A of nucleic acid Q under hybridisation conditions, the at least one diagnostic oligonucleotide containing at least one LNA,
   e) repeating steps c) and d) a sufficient number of times to result in a detectable amount of extension products,
   f) detecting the extension products formed.

3. A method for detecting in a sample the presence of a nucleic acid Q' whose nucleotide sequence differs from a nucleic acid Q in at least one position A, the method comprising the steps of
   a) combining nucleic acids present in the sample with an appropriate amount of nucleoside triphosphates, an agent for polymerisation of the nucleoside triphosphates, at least one downstream oligonucleotide and at least one diagnostic oligonucleotide containing at position A a nucleotide which is capable of hybridising to the nucleotide at position A of nucleic acid Q' but not to a nucleotide ay position A of nucleic acid Q hybridisation conditions, the at least one diagnostic oligonucleotide containing at least one LNA,
   b) extending any oligonucleotides which hybridize to the nucleic acids present in the sample to form extension products, wherein said nucleic acids are used as templates,
   c) after the formation of extension products treating the reaction mixture under denaturing conditions to separate the extension products from the template,
   d) hybridising in the presence of an appropriate amount of nucleoside triphosphate and an agent for polymerisation of the nucleoside triphosphates the single stranded nucleic acids of step c) with at least one diagnostic oligonucleotide containing at position A a nucleotide which is capable of hybridizing to the nucleotide at position A of nucleic acid Q' but not to a nucleotide at position A of nucleic acid Q under hybridisation conditions, the at least one diagnostic oligonucleotide containing at least one LNA,
   e) repeating steps c) and d) a sufficient number of times to result in a detectable amount of extension products,
   f) detecting the extension products formed.

4. A method for detecting target nucleic acids whose nucleotide sequences differ from one another in at least one position A, the method comprising the steps of
   a) combining the nucleic acids with an appropriate amount of nucleoside triphosphates, an agent for polymerisation of the nucleoside triphosphates and at least one set of diagnostic oligonucleotides under hybridisation conditions, the at least one set of diagnostic oligonucleotides having nucleotide sequences which differ from one another in at least one position A and contain at least one LNA,
   b) extending any oligonucleotides which hybridize to the nucleic acids to form extension products, wherein said nucleic acids are used as templates,
   c) detecting the nucleic acids formed in step b).

5. A method for detecting target nucleic acids whose nucleotide sequences differ from one another in at least one position A, the method comprising the steps of a) combining the nucleic acids with an appropriate amount of nucleoside triphosphates, an agent for polymerisation of the nucleoside triphosphates and at least one set of diagnostic oligonucleotides under hybridisation conditions, the at least one set of diagnostic oligonucleotides having nucleotide sequences which differ from one another in at least one position A and contain at least one LNA, b) extending any oligonucleotides which hybridize to the nucleic acids to form extension products, wherein said nucleic acids are used as templates, c) after the formation of extension products treating the reaction mixture under denaturing conditions to separate the extension products from the template, d) hybridising in the presence of an appropriate amount of nucleoside triphosphates and an agent for polymerisation of the nucleoside triphosphates the single stranded nucleic acids from step c) with at least one set of diagnostic oligonucleotides whose nucleotide sequences differ from one another in at least one position A to synthesise further extension products, e) repeating steps c) and d) a sufficient number of times to result in a detectable amount of extension products, f) detecting the extension products formed.

6. A method for detecting target nucleic acids whose nucleotide sequences differ from one another in at least one position A, the method comprising the steps of a) combining the nucleic acids with an appropriate amount of nucleoside triphosphates, an agent for polymerisation of the nucleoside triphosphates, at least one downstream oligonucleotide and at least one set of diagnostic oligonucleotides under hybridisation conditions, the at least one set of diagnostic oligonucleotides having nucleotide sequences which differ from one another in at least one position A and contain at least one LNA, b) extending any oligonucleotides which hybridize to the nucleic acids to form extension products, wherein said nucleic acids are used as templates, c) after the formation of extension products treating the reaction mixture under denaturing conditions to separate the extension products from the template, d) hybridising in the presence of an appropriate amount of nucleoside triphosphates and an agent for polymerisation of the nucleoside triphosphates the single stranded nucleic acids step c) with at least one downstream oligonucleotide and at least one set of diagnostic oligonucleotides being oligonucleotides whose nucleotide sequences differ from one another in at least one position A to synthesise further extension products, e) repeating steps c) and d) a sufficient number of times to result in a detectable amount of extension products, f) detecting the extension products formed.

7. A method for detecting target nucleic acids whose nucleotide sequences differ from one another in at least one position A, the method comprising the steps of a) combining the target nucleic acids with an appropriate amount of nucleoside triphosphates, at least two oligonucleotides wherein at least one of said oligonucleotides is a diagnostic oligonucleotide and an agent for ligation of the oligonucleotides under hybridisation conditions, the at least one diagnostic oligonucleotide being an oligonucleotide containing at position A a nucleotide which is complementary to the nucleotide found at position A of the target nucleic acid to be detected, said diagnostic oligonucleotide contains at least one LNA, b) ligating any oligonucleotides which hybridize to the nucleic acids at adjacent positions to form ligation products, wherein said nucleic acids are used as templates, c) detecting the nucleic acids formed in step b).

8. A method for detecting target nucleic acids whose nucleotide sequences differ from one another in at least one position A, the method comprising the steps of a) combining the target nucleic acids with an appropriate amount of nucleoside triphosphates, at least two oligonucleotides wherein at least one of said oligonucleotides is a diagnostic oligonucleotide and an agent for ligation of the oligonucleotides under hybridisation conditions, the at least one diagnostic oligonucleotide being an oligonucleotide containing at position A a nucleotide which is complementary to the nucleotide found at position A of the target nucleic acid to be detected, said diagnostic oligonucleotide contains at least one LNA, b) ligating any oligonucleotides which hybridize to the nucleic acids at adjacent positions to form ligation products, wherein said nucleic acids are used as templates, c) treating the reaction mixture under denaturing conditions to separate the ligation products from the template after the ligation, d) hybridising in the presence of an appropriate amount of nucleoside triphosphates and an agent for ligation of the oligonucleotides under hybridisation conditions the single stranded nucleic acids from step c) with at least one oligonucleotide being complementary to the ligation product from step b) and at least two oligonucleotides the at least one diagnostic oligonucleotide being an oligonucleotide containing at position A a nucleotide which is complementary to the nucleotide found at position A of the target nucleic acid to be detected, said diagnostic oligonucleotide contains at least one LNA, e) repeating steps c) and d) a sufficient number of times to result in a detectable amount of ligation products, f) detecting the ligation products formed.

9. A method according to claim 1, 2, 3, 4, 5, 6, 7 or 8, wherein the at least one position A of the diagnostic oligonucleotide sequence is complementary to position A of the nucleic acid sequence to be detected but not to position A of the other nucleic acid sequences.

10. A method according to claim 1, 2, 3, 4, 5, 6, 7, or 8, wherein the nucleotide at the at least one position A in the diagnostic oligonucleotide is a LNA.

11. A method according to claim 1, 2, 3, 4, 5, 6, 7, or 8, wherein the diagnostic oligonucleotide has the general formula $$5'\text{-Nu}_a(\text{NU}_b\text{LNA}_c)_m\text{Nu}_d\text{A}_e\text{Nu}_f\text{-}3'$$

where A is a LNA position in which the variant nucleic acid sequences of the target nucleic acids differs from one another; LNA is a LNA; Nu is a monomer selected from the group consisting of any nucleotides other than LNA capable of forming specific base-pairs with the variqant nucleic acids; a, b, c, d anf f are integers between 0 and 30, m is an integer between 1 and 8 and e is an integer between 1 and 6 with the proviso that the sum of a, b, c, d, e and f is at least 5.

12. A method according to claim 11, wherein a=10, b=0, c=4, d=8, e=1, f=0, m=0 in the general formula a.

13. A method according to claim 11, wherein a=0, b=1, c=1, d=8, e=1, f=0, m=5 in the general formula a.

14. A method according to claim 11, wherein a=10–30, b=0, c=0, d=0, e=1–4, f=1–8, m=0 in the general formula a.

15. A method according to claim 11, wherein a=10–30, b=0, c=0, d=0, e=1–4, f=1, m=0 in the general formula a.

16. A method according to claim 11, wherein a=10–30, b=0, c=0, d=0, e=1–4, f=0, m=0 in the general formula a.

17. A method according to claim 11, wherein a=10–30, b=0, c=0, d=0, e=1, f=0, m=0 in the general formula a.

18. A method according to claim 11, wherein a=10, b=0, c=0, d=0, e=4, f=8, m=0 in the general formula a.

19. A method according to claim 11, wherein a=24, b=0, c=0, d=0, e=1, f=0, m=0 in the general formula a.

20. A method according to claim 1, 2, 3, 4, 5, 6, 7, or 8, wherein the at least one diagnostic oligonucleotide is covalently attached to a solid support.

21. A method according to claim 20, wherein the different diagnostic oligonucleotides are spotted in an array format on the solid surface.

22. A method according to claim 1, 2, 3, 4, 5, 6, 7, or 8, wherein the different downstream oligonucleotide are spotted in an array format on the solid surface.

23. A method according to claim 20, wherein the attachment is performed by the anthraquinone photochemistry.

24. A method according to claim 20, wherein the at least one diagnostic oligonucleotide is labelled with a detectable group.

25. A method according to claim 4, wherein the at least one first set of diagnostic oligonucleotides is labelled with detectable groups, said detectable groups being different for the different diagnostic oligonucleotides.

26. A method according to claim 25, wherein the individual oligonucleotides in each oligonucleotide set is labelled with detectable groups, said detectable groups being different for the each individual diagnostic oligonucleotide.

27. A method according to any of claims 1–8, wherein said target nucleic acids to be detected originate from a sample of cells, a tissue sample or a tissue extract.

28. A method according to claim 27, wherein the cells are of archae, prokaryotic or eukaryotic origin.

29. A method according to claim 27, wherein the sample of cells is derived from blood, serum, plasma, reticulocytes, lymphocytes, urine, bone marrow tissue, cerebrospinal fluid or any product prepared from blood or lymph.

30. A method according to claim 27, wherein the tissue sample is derived from muscle biopsy, liver biopsy, kidney biopsy, bladder biopsy, bone biopsy, cartilage biopsy, skin biopsy, pancreas biopsy, a biopsy of the intestinal tract, thymus biopsy, mammae biopsy, uterus biopsy, testicular biopsy, eye biopsy or brain biopsy.

31. A method according to any of claims 28–30, wherein said target nucleic acids to be detected are at least one sequence specific for a particular species of organism.

32. A method according to any of claims 28–30, wherein said target nucleic acids to be detected are at least one sequence specific for a particular species, sub-species or strains of organisms.

33. A method according to any of claims 28–30, wherein said target nucleic acids to be detected are at least one sequence specific for a particular species of micro-organisms.

34. A method according to any of claims 28–30, wherein said target nucleic acids to be detected are at least one sequence specific for a particular species, sub-species or strains of micro-organisms.

35. A method according to any of claims 28–30, wherein said target nucleic acids to be detected are at least one sequence specific for a particular infectious agent.

36. A method according to any of claims 28–30, wherein said target nucleic acids to be detected are at least one sequence specific for a particular species, sub-species or strain of infectious agents.

37. A method according to any of claims 28–30, wherein said target nucleic acids to be detected are at least one sequence specific for genes coding for particular proteins involved in inheritable diseases.

38. A method according to any of claims 28–30, wherein said target nucleic acids to be detected are at least one sequence specific for a gene related to a life style disease.

39. A method according to any of claims 28–30, wherein said target nucleic acids to be detected are at least one sequence specific for a particular gene related to cancer.

40. A method according to claim 38, wherein the life style disease is selected from the group consisting of obesity, familial hypercholesterolaemia, atherosclerosis and diabetes.

41. A method according to claim 27, wherein said target nucleic acids to be detected are alleles.

42. A method according to any of claims 1–6, wherein the agent for polymerization is an enzyme.

43. A method according to claim 42, wherein the agent for polymerization is a DNA polymerase.

44. A method according to claim 43, wherein the agent for polymerization is a thermostable DNA polymerase.

45. A method according claim 44, wherein the thermostable DNA polymerase is selected from the group consisting of Taq, Pfu, Pwo and Tth.

46. A method according to claim 42, wherein the agent for polymerization is a RNA polymerase.

47. A method according to any of claims 7–8, wherein the agent for ligation is an enzyme.

48. A method according to claim 47, wherein the agent for ligation is a ligase.

\* \* \* \* \*